(12) United States Patent
Chhatkuli et al.

(10) Patent No.: US 12,138,073 B2
(45) Date of Patent: Nov. 12, 2024

(54) PREDICTING BODY COMPOSITION FROM USER IMAGES USING DEEP LEARNING NETWORKS

(71) Applicant: Bodygram, Inc., New York, NY (US)

(72) Inventors: Subas Chhatkuli, Tokyo (JP); Kyohei Kamiyama, Tokyo (JP); Chong Jin Koh, Las Vegas, NV (US)

(73) Assignee: Bodygram, Inc., Dover, DE (US)

( * ) Notice: Subject to any disclaimer, the term of this patent is extended or adjusted under 35 U.S.C. 154(b) by 0 days.

(21) Appl. No.: 18/548,911

(22) PCT Filed: Mar. 24, 2022

(86) PCT No.: PCT/US2022/021637
§ 371 (c)(1),
(2) Date: Sep. 4, 2023

(87) PCT Pub. No.: WO2022/204343
PCT Pub. Date: Sep. 29, 2022

(65) Prior Publication Data
US 2024/0148321 A1 May 9, 2024

Related U.S. Application Data

(60) Provisional application No. 63/165,161, filed on Mar. 24, 2021.

(51) Int. Cl.
| | |
|---|---|
| A61B 5/00 | (2006.01) |
| A61B 5/107 | (2006.01) |
| G06V 10/82 | (2022.01) |
| G06V 40/16 | (2022.01) |
| G16H 10/60 | (2018.01) |

(52) U.S. Cl.
CPC .......... *A61B 5/4869* (2013.01); *A61B 5/1072* (2013.01); *A61B 5/1079* (2013.01);
(Continued)

(58) Field of Classification Search
CPC ..... A61B 5/1077; A61B 5/107; A61B 5/1073; A61B 5/4519; A61B 5/4869;
(Continued)

(56) References Cited

U.S. PATENT DOCUMENTS 9,788,759 B2 * 10/2017 Ferrantelli ........... A61B 5/0077
9,936,754 B2 *  4/2018 Koh ................... G01B 11/2513
(Continued)

FOREIGN PATENT DOCUMENTS

WO    WO-2020132713 A1 *  7/2020 .......... A61B 5/0013
WO       2021178632 A1      9/2021

*Primary Examiner* — Manav Seth
(74) *Attorney, Agent, or Firm* — American Patent Agency PC; Daniar Hussain; Stephen M. Hou

(57) ABSTRACT

Systems and methods for generating a prediction of a body composition of a user using an image capturing device are disclosed. The systems and methods can be used to predict body compositions such as body fat percentage, water content percentage, muscle mass, bone mass, and so on, from a single user image. The methods include the steps of receiving one or more user images and one or more user parameters, generating one or more key points based on the one or more user images, and generating a prediction of the body composition of the user based on the one or more key points and the one or more user parameters, using a body composition deep learning network (DLN). In one embodiment, the body composition DLN comprises a face image DLN, a body feature DLN, and an output DLN.

18 Claims, 12 Drawing Sheets

(52) U.S. Cl.
CPC ............ *G06V 10/82* (2022.01); *G06V 40/168* (2022.01); *G16H 10/60* (2018.01); *G06V 2201/03* (2022.01)

(58) Field of Classification Search
CPC .... A61B 5/1072; A61B 5/1079; G16H 10/60; G06V 40/168; G06V 10/82; G06V 2201/03

See application file for complete search history.

(56) References Cited

U.S. PATENT DOCUMENTS

| | | | |
|---|---|---|---|
| 10,321,728 B1* | 6/2019 | Koh | G06T 7/11 |
| 10,335,572 B1* | 7/2019 | Kumar | G06F 3/015 |
| 10,470,510 B1* | 11/2019 | Koh | G06T 17/10 |
| 10,489,683 B1* | 11/2019 | Koh | G06N 20/20 |
| 10,636,158 B1* | 4/2020 | Kamiyama | G06T 7/50 |
| 10,918,150 B2* | 2/2021 | Koh | G05B 19/4097 |
| 10,962,404 B2* | 3/2021 | Kamiyama | G06N 20/00 |
| 11,017,547 B2* | 5/2021 | Ferrantelli | G06V 10/82 |
| 11,069,131 B2* | 7/2021 | Agrawal | G06T 17/00 |
| 11,423,630 B1* | 8/2022 | Agrawal | G06T 7/55 |
| 11,836,853 B2* | 12/2023 | Agrawal | G06T 15/005 |
| 11,903,730 B1* | 2/2024 | Chaudhri | G06T 7/194 |
| 2015/0223730 A1* | 8/2015 | Ferrantelli | A61B 5/1072 382/154 |
| 2018/0289334 A1* | 10/2018 | De Brouwer | G06N 5/046 |
| 2020/0345314 A1 | 11/2020 | Fedewa et al. | |
| 2022/0198696 A1* | 6/2022 | Jones | G06T 7/62 |
| 2023/0052613 A1* | 2/2023 | Kamiyama | G06V 40/103 |

* cited by examiner

| Actual body composition | | Predicted body composition | |
|---|---|---|---|
| SLM (Soft Lean Mass) | PBF (Percent Body Fat) | Predicted SLM | Predicted PBF |
| 33.3 | 28.3 | 35.732643 | 25.565351 |
| 31.2 | 24.5 | 33.29882 | 21.421019 |
| 32.9 | 21.8 | 31.47435 | 25.412157 |
| 31.2 | 24.5 | 33.14825 | 21.393372 |
| 31.2 | 24.5 | 32.924587 | 21.535364 |
| 31.2 | 24.5 | 33.021946 | 21.349802 |
| 32.6 | 25.8 | 32.62331 | 26.922941 |
| 31.2 | 24.5 | 32.995476 | 21.264555 |
| 31.2 | 24.5 | 32.886875 | 21.551155 |
| 33.7 | 22.8 | 31.879726 | 26.030806 |
| 31.2 | 24.5 | 32.993732 | 21.460531 |
| 33.7 | 22.8 | 31.918175 | 26.072477 |
| 31.2 | 24.5 | 32.847324 | 21.885017 |
| 32.9 | 21.8 | 31.433361 | 25.721972 |
| 32.6 | 25.8 | 33.054302 | 26.790085 |

*FIG. 9*

Accuracy plot of predicted SLM

Accuracy plot of predicted PBF

PREDICTING BODY COMPOSITION FROM USER IMAGES USING DEEP LEARNING NETWORKS

FIELD OF THE INVENTION

Embodiments of the present invention are in the field of automated body feature measurements and pertain particularly to generating a prediction of a body composition of a user using images taken with an image capturing device.

BACKGROUND OF THE INVENTION

The background of the invention is provided merely to help understand the context of the invention and its application and uses, and may not be considered prior art.

Body composition provides information about individual health and wellness. A measurement of body composition is a quantitative measurement of one or more individual components constituting the body of a human (or any other living organism). Body composition may be defined as a quantitative indicator of one of the body's constituent components, such as body fat, muscle, bone, water, etc. Such indicators include weight, volume, and proportions or percentages thereof. For example, obesity, a medical condition that involves the accumulation of excess body fat, may be assessed through body mass index (BMI), which is an indicator of body fatness based upon an individual's weight and height. Obesity may also be assessed through a number of other indicators such as Percent Body Fat (PBF). "Body composition", "body composition prediction" and "body composition measurement" are used interchangeably herein.

Some existing systems to measure body composition utilize depth images obtained from a 3D scanned body to predict body fat. Usually, the user has to wear reduced clothing (e.g., undergarments) for an accurate BMI measurement. At a time when speedy services through smartphone applications are becoming ubiquitous, the requirement for 3D scans and/or reduced user clothing is costly and cumbersome.

Other systems to measure body composition utilize frontal face images of a user to predict height, weight, and BMI. Many systems measure body composition using statistical data or based on a single type of data (e.g., face image), hence delivering predictions that lack robustness and accuracy. Therefore, there is a need for a system that can accurately measure body composition by combining user images with other inputs such as user parameters (e.g., user height or gender).

It is against this background that various embodiments of the present invention were developed.

BRIEF SUMMARY OF THE INVENTION

This summary of the invention provides a broad overview of the invention, its application, and uses, and is not intended to limit the scope of the present invention, which will be apparent from the detailed description when read in conjunction with the drawings.

The present invention relates to methods and systems for generating a prediction of user's body composition using user images and one or more user parameters. The user images and parameters may be obtained through an image-capturing device such as a mobile smartphone.

In one embodiment, the present invention is a computer-implemented method for predicting a body composition of a user, the method including receiving one or more user images and one or more user parameters, generating one or more key points based on the one or more user images, and generating a prediction of the body composition of the user based on the one or more key points and the one or more user parameters, using a body composition deep learning network (DLN). In one embodiment, generating one or more key points includes using a key point DLN.

In one embodiment, the body composition DLN includes a face image DLN configured to receive a face image of the user and to generate a face feature vector; a body feature DLN configured to receive the one or more user parameters and a set of one or more scaled external body feature dimensions, and to generate a body feature vector; and an output DLN configured to receive the face feature vector and the body feature vector, and to generate the body composition of the user.

In another embodiment, the face image DLN is a Convolutional Neural Network (CNN), and the body feature DLN and the output DLN are fully connected neural networks.

In one embodiment, the body composition is an indicator of muscle, bone, water content, or body fat of the user.

In one embodiment, the body composition is selected from the group consisting of a Lean Body Mass (LBM), a Mass Body Fat (MBF), a Soft Lean Mass (SLM), and a Percent Body Fat (PBF).

In one embodiment, the one or more user parameters are selected from the group consisting of a height, a weight, a gender, and an age.

In another embodiment, the computer-implemented method further includes extracting a head image of the user from the one or more user images, wherein generating the body composition using the body composition DLN is further based on the head image.

In one embodiment, the head image is a face image, and wherein the face image is extracted using one of a face extraction computer vision module and a face extraction DLN.

In some embodiments, the one or more user images include at least a front image and a side image.

In one embodiment, the one or more user images represent a fully clothed user.

In another embodiment, the computer-implemented method further includes generating a height of the user from the one or more user images, and utilizing the height as one of the user parameters.

In yet another embodiment, the computer-implemented method further includes generating a weight of the user from the one or more user images, and utilizing the weight as one of the user parameters.

In one embodiment, the computer-implemented method further includes generating a set of one or more scaled external body feature dimensions based on the one or more key points, wherein generating the body composition using the body composition DLN is further based on the set of one or more scaled external body feature dimensions.

In one embodiment, generating the set of one or more scaled external body feature dimensions includes generating a set of one or more external body feature dimensions from the one or more key points, and scaling the set of one or more external body feature dimensions to generate the set of one or more scaled external body feature dimensions.

In some embodiments, scaling the set of one or more external body feature dimensions uses a scale factor determined using one of (a) an object of known size captured on one of the user images, (b) a depth sensor, (c) a Lidar, (d) distances between at least three feature points of a ground plane detected using an augmented reality software development kit (AR-SDK), and (e) a height received from the user and a pixel height determined from one of the front image and the side image of the user.

In other embodiments, the one or more external body feature dimensions are selected from the group consisting of a height, a belly depth, a belly length, a belly waist, a bust girth, a hip girth, a neck girth, a thigh girth, an under bust girth, an upper arm girth, a waist girth, and a wrist girth.

In some embodiments, the present invention is a non-transitory, computer-readable storage medium storing executable instructions, which when executed by a processor, causes the processor to perform a process for predicting a body composition of a user, the instructions causing the processor to perform the aforementioned steps.

In other embodiments, a computer program product is disclosed. The computer program may be used for predicting a body composition of a user, and may include a computer-readable storage medium having program instructions, or program code, embodied therewith, the program instructions executable by a processor to cause the processor to perform the aforementioned steps.

In various embodiments, a system is described, including a memory that stores computer-executable components, and a hardware processor, operably coupled to the memory, and that executes the computer-executable components stored in the memory, where the computer-executable components may include components communicatively coupled with the processor that execute the aforementioned steps.

In one embodiment, the present invention is a system for predicting a body composition of a user, the system comprising a user device having a 2D camera, a processor, a display, a first memory; a server comprising a second memory and a data repository; a telecommunications-link between said user device and said server; and a plurality of computer codes embodied on said first and second memory of said user-device and said server, said plurality of computer codes which when executed causes said server and said user-device to execute a process comprising the aforementioned steps.

In other embodiments, the present invention is a computerized server comprising at least one processor, memory, and a plurality of computer codes embodied on said memory, said plurality of computer codes which when executed causes said processor to execute a process comprising the aforementioned steps. Other aspects and embodiments of the present invention include the methods, processes, and algorithms comprising the steps described herein, and also include the processes and modes of operation of the systems and servers described herein.

Yet other aspects and embodiments of the present invention will become apparent from the detailed description of the invention when read in conjunction with the attached drawings.

BRIEF DESCRIPTION OF THE DRAWINGS

The accompanying drawings, which are incorporated in and constitute part of this specification, illustrate embodiments of the invention and together with the description, serve to explain the principles of the disclosed embodiments. For clarity, simplicity, and flexibility, not all elements, components, or specifications are defined in all drawings. Not all drawings corresponding to specific steps or embodiments of the present invention are drawn to scale. Emphasis is instead placed on illustration of the nature, function, and product of the methods and devices described herein.

Embodiments of the present invention described herein are exemplary, and not restrictive. Embodiments will now be described, by way of examples, with reference to the accompanying drawings, in which:

FIG. 9 is a table showing the performance of one embodiment of a body composition DLN that uses the illustrative body composition prediction architecture of FIGS. 7A and 7B in generating the Soft Lean Mass (SLM) and Percent Body Fat (PBF) of a user.

DETAILED DESCRIPTION OF THE INVENTION

Figure 1:
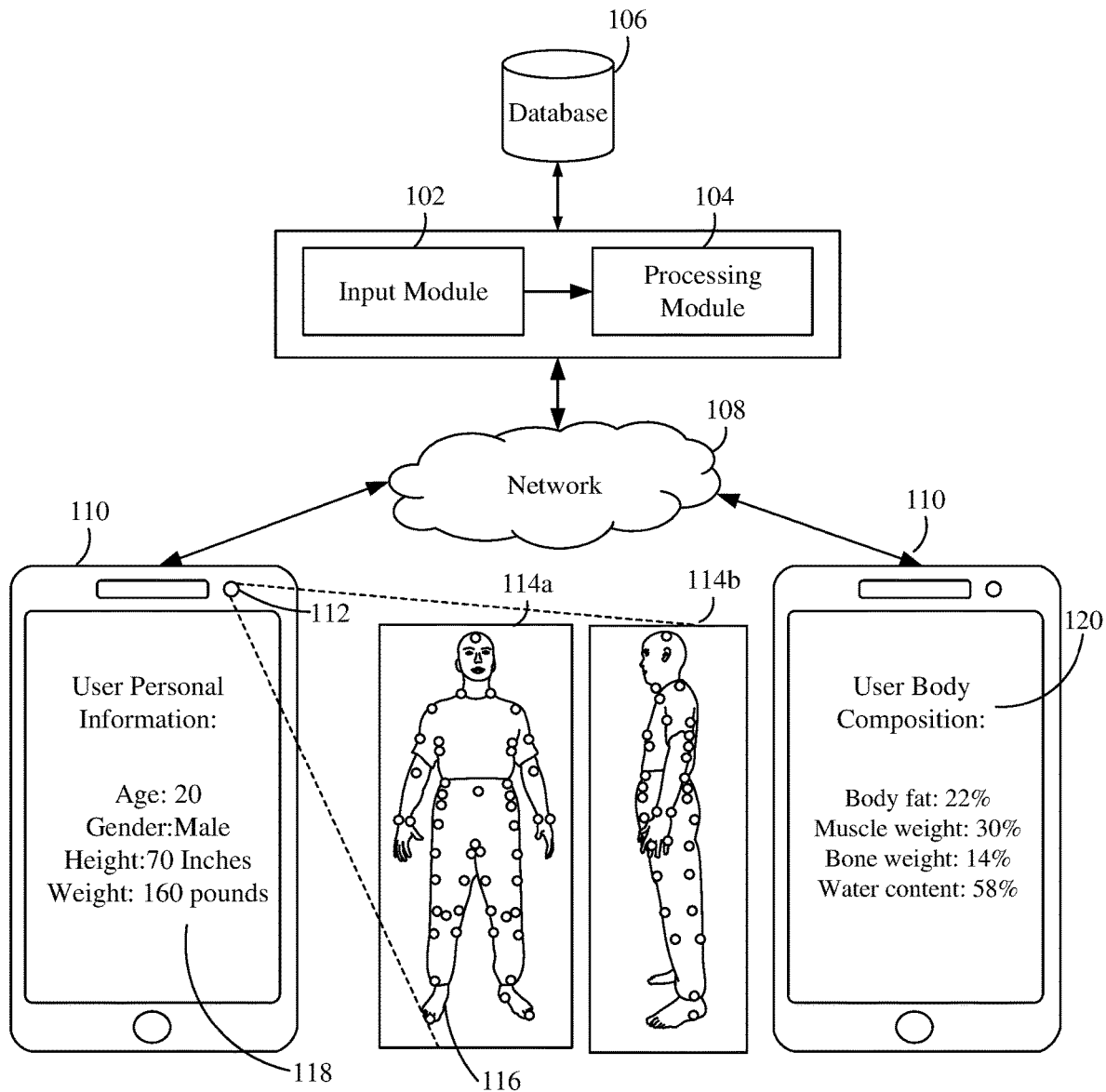
FIG. 1 illustrates a block diagram of a system for predicting the body composition of a user, according to a preferred embodiment of the present invention.

The present invention will be more completely understood through the following detailed description which should be read in conjunction with the attached drawing in which similar reference numbers indicate similar structures. All references cited above and in the following description are hereby expressly incorporated by reference.

Reference will now be made in detail to the exemplary embodiment(s) of the invention. References to "one embodiment," "at least one embodiment," "an embodiment," "one example," "an example," "for example," and so on indicate that the embodiment(s) or example(s) may include a particular feature, structure, characteristic, property, element, or limitation but that not every embodiment or example necessarily includes that particular feature, structure, characteristic, property, element, or limitation. Further, repeated use of the phrase "in an embodiment" does not necessarily refer to the same embodiment.

In the following description, for purposes of explanation, numerous specific details are set forth in order to provide a thorough understanding of the invention. It will be apparent, however, to one skilled in the art that the invention can be practiced without these specific details. In other instances, structures, devices, activities, methods, and processes are shown using schematics, use cases, and/or diagrams in order to avoid obscuring the invention. Although the following description contains many specifics for the purposes of illustration, anyone skilled in the art will appreciate that many variations and/or alterations to suggested details are within the scope of the present invention. Similarly, although many of the features of the present invention are described in terms of each other, or in conjunction with each other, one skilled in the art will appreciate that many of these features can be provided independently of other features. Accordingly, this description of the invention is set forth without any loss of generality to, and without imposing limitations upon, the invention.

As used herein, the singular forms "a," "an," and "the" include plural references unless the context clearly indicates otherwise. Also as used herein, the term "about" in connection with a measured quantity, refers to the normal variations in that measured quantity, as expected by one of ordinary skill in the art in making the measurement and exercising a level of care commensurate with the objective of measurement and the precision of the measuring equipment. In certain embodiments, the term "about" includes the recited number+/−10%, such that "about 10" would include from 9 to 11.

BODYGRAM is a trademark name carrying embodiments of the present invention, and hence, the aforementioned trademark name may be used in the specification and drawing to refer to the products/manufacturing process offered by embodiments of the present invention. The term BODYGRAM and its equivalents may be used interchangeably in this specification to describe the present invention, as well as the company providing said invention. With reference to the figures, embodiments of the present invention are now described in detail.

Overview

Different approaches have been used to measure body composition from images of users. Previous approaches generally require the user to have specific poses, stand at a specific distance from the camera, in front of an empty background, wear a tight-fitting shirt, and/or go partially nude, wearing only underwear. Such requirements for controlled environments and significant user friction are undesirable.

Embodiments of the present invention provide systems and methods configured to estimate body composition by using at least one image of a user, the user's body key points (e.g., obtained from a fully clothed image of the user), and at least one user parameter (e.g., age, height, etc.). One embodiment of the present invention provides systems and methods configured to estimate body composition by using a frontal face image of a user, the user's body key points (e.g., obtained from a fully clothed front image and side image), and one or more user parameters.

The present invention provides a system and method for accurately measuring body composition from 2D images (e.g., RGB-red green blue, RGB-D red green blue depth, or Grayscale images) with a user wearing any type of clothing, and the images taken at any distance, such that any user can easily take images of themselves and measure their body composition. Advanced computer vision and deep learning techniques are used to estimate the body composition of the user, no matter what the user is wearing, from images provided from an image capturing device. Some embodiments of the present invention leverage the AR (augmented reality) SDK (software development kit) provided in the image-capturing devices. In the present disclosure, the term "image capturing device" is used to represent any cameras embedded in, or connected to, computing devices, such as smartphones, tablets, laptops, or desktops.

Various embodiments of the present invention combine multiple data types such as user images, generated key points, received or generated user parameters such as age, gender, height, or weight, and other statistical data (e.g., a database of body heights classified by age and/or gender) to generate one or more predictions of the user's body composition. Each of the input data types may possess useful information to estimate body composition as well as weaknesses (e.g., biases) that may lead to inaccurate predictions of body composition. By meaningfully combining information from more than one data type, such embodiments of the present invention compensate for the weaknesses inherent to some data types, hence producing more accurate prediction results.

FIG. 1 illustrates a block diagram of a system for measuring the body composition (120) of the user (116), according to a preferred embodiment of the present invention. The system includes an image capturing device (110), a server, and a network (108), where the server includes an input module (102), a processing module (104), and a database (106). The image capturing device (110) includes a camera (112) that captures at least one image of the user. In FIG. 1, the camera (112) captures a front image (114a) and a side image (114b) of the user (116). The front image (114a) and the side image (114b) of the user (116) may represent a fully-clothed user, as in FIG. 1. However, the user image(s) (114a and/or 114b) may show the user in undergarments only, in tight clothing, or nude. The user image(s) (114a and/or 114b) usually show the entire body of the user (116). Although a front image and a side image are represented in FIG. 1, one image is sufficient to predict body composition according to one embodiment of the present invention.

The image capturing device (110) may be one of a smartphone, a camera, a tablet, a laptop, a desktop, and a scanner, although the image capturing device (110) is not limited to listed devices. The image capturing device (110) is configured to receive one or more user parameters (118) such as an age, a gender, a height, and a weight of the user (116). The input module (102) is configured to receive the front image (114a) and/or the side image (114b) of the user, and the one or more user parameters (118), through a network (108) from the image capturing device (110).

The network (108) may include wireless communication links using a technology such as shortwave, microwave, high frequency, wireless fidelity (Wi-Fi), Bluetooth, global system for mobile communications (GSM), code division multiple access (CDMA), second-generation (2G), third-generation (3G), fourth-generation (4G), 4G long term evolution (LTE), LTE Advanced, or any other wireless communication technology or standard to establish a wireless communication for exchanging data. In another embodiment, the front image (114a), the side image (114b) of the user, or the one or more user parameters (118) may be obtained from the database (106). The one or more user parameters may be determined automatically (e.g., using computer vision algorithms based on the front (114a) or side (114b) images, or other user images, or mined from one or more databases), or determined from the user (e.g., user input).

In some embodiments, the processing module (104) is configured to identify one or more annotation key points for one or more body parts underneath clothing of the user (116) from the front image (114a) or the side image (114b), using a key point deep-learning module or deep learning network (DLN), compute a set of one or more external body feature dimensions of the user (116) based on the one or more annotation key points, derive a scale factor based on the one or more user parameters (118) and the one or more annotation key points, and compute a set of one or more scaled external body feature dimensions of the user (116) based on the set of one or more external body feature dimensions and the scale factor.

Advanced computer vision combined with deep-learning techniques are used to identify one or more annotation key points for one or more body parts. The expressions "annotation key point" and "key point" are henceforth used interchangeably.

The scale factor is used to scale from pixel dimensions in the front image and/or the side image of the user to real-world dimensions of the user. In one embodiment, the scale factor is derived based on a height (i.e., one or more user parameters) received from the user and a pixel height (i.e., the one or more annotation key points) determined from at least one of the front image and the side image of the user.

The set of one or more external body feature dimensions may be selected from the group consisting of a height, a belly depth, a belly length, a belly waist, a bust girth, a hip girth, a neck girth, a thigh girth, an underbust girth, an upper arm girth, a waist girth, and a wrist girth, associated with the user. The set of one or more external body feature dimensions is used to compute the set of one or more scaled external body feature dimensions, as shown in FIG. 2.

In some embodiments, the processing module (104) is configured to extract a user's head image from an image of the user through a computer vision module, where generating the body composition using the body composition DLN is further based on the head image. Further, the processing module (104) may be configured to trigger a head image DLN to receive the user's head image and generate a user's head feature vector from the user's head image, where generating the body composition using the body composition DLN is further based on the head feature vector.

In one illustrative embodiment, the processing module (104) is configured to extract a user's face image from the front image (114a) of the user (116) using a face extraction computer vision module. Further, the processing module (104) is configured to trigger a face image deep learning module to receive the user's face image and generate a user's face feature vector from the user's face image. The face image deep learning module may be a Convolutional Neural Network (CNN). However, the use of any other neural network, machine learning (ML), or artificial intelligence (AI) module to generate a face feature vector is within the scope of the present invention. In one embodiment, the processing module (104) is configured to extract a user's face image from a front image of the user using the dlib open source machine vision library.

Figure 2:
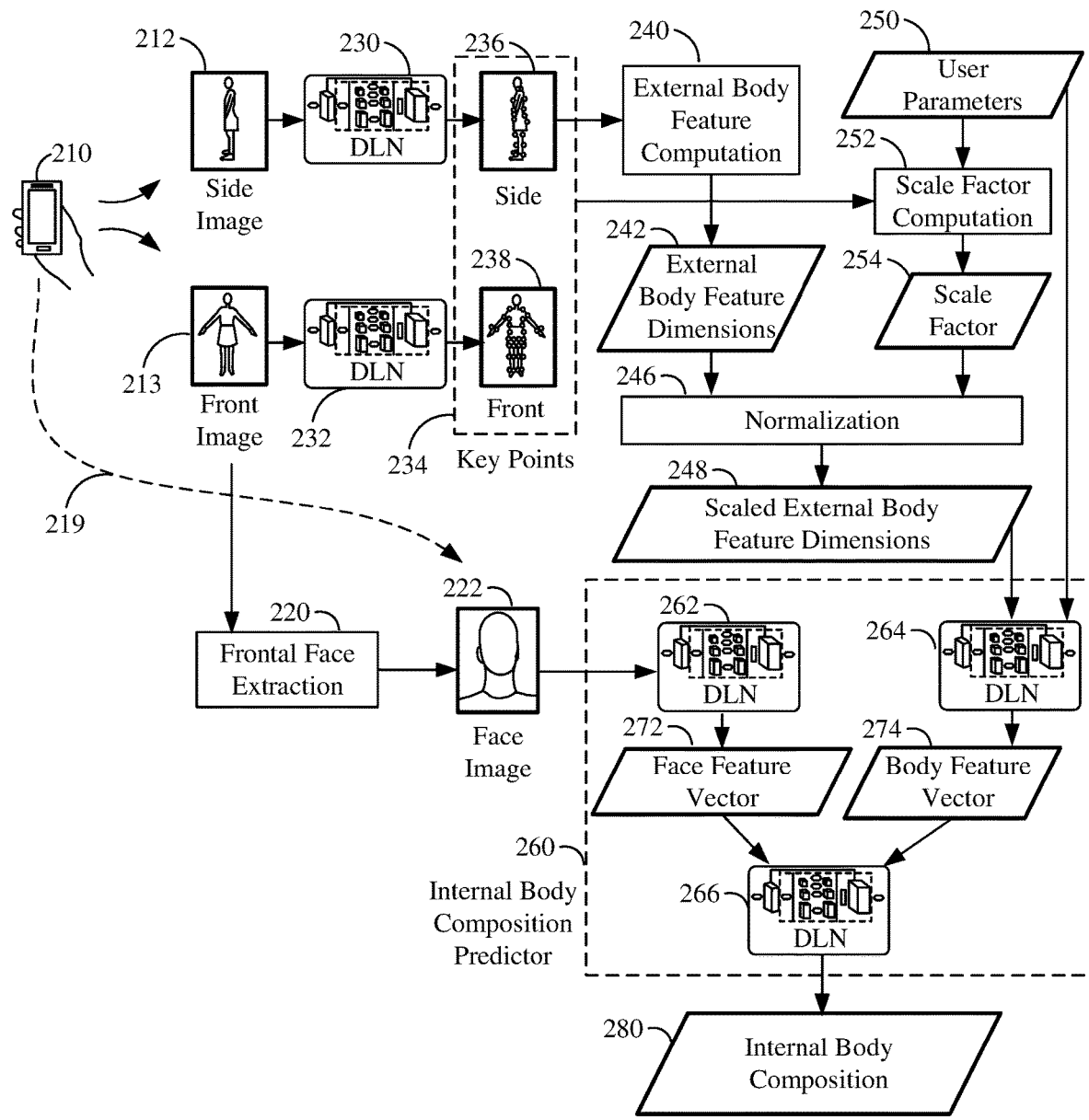
FIG. 2 illustrates an example block diagram for predicting the body composition of the user through deep learning, in accordance with one embodiment of the present invention.

Further, the processing module (104) is configured to trigger a body feature deep learning module to receive the set of one or more scaled external body feature dimensions of the user (116) and the one or more user parameters (118) and generate a user's body feature vector from the set of one or more scaled external body feature dimensions of the user (116) and the one or more user parameters (118), as illustrated in FIG. 2.

Moreover, the processing module (104) is configured to trigger an output deep learning module to receive the user's face feature vector from the face image deep learning module and the user's body feature vector from the body feature deep learning module and generate a prediction of the body composition (120) of the user based on the user's face feature vector and the user's body feature vector, as illustrated in FIG. 2.

Figure 7A:
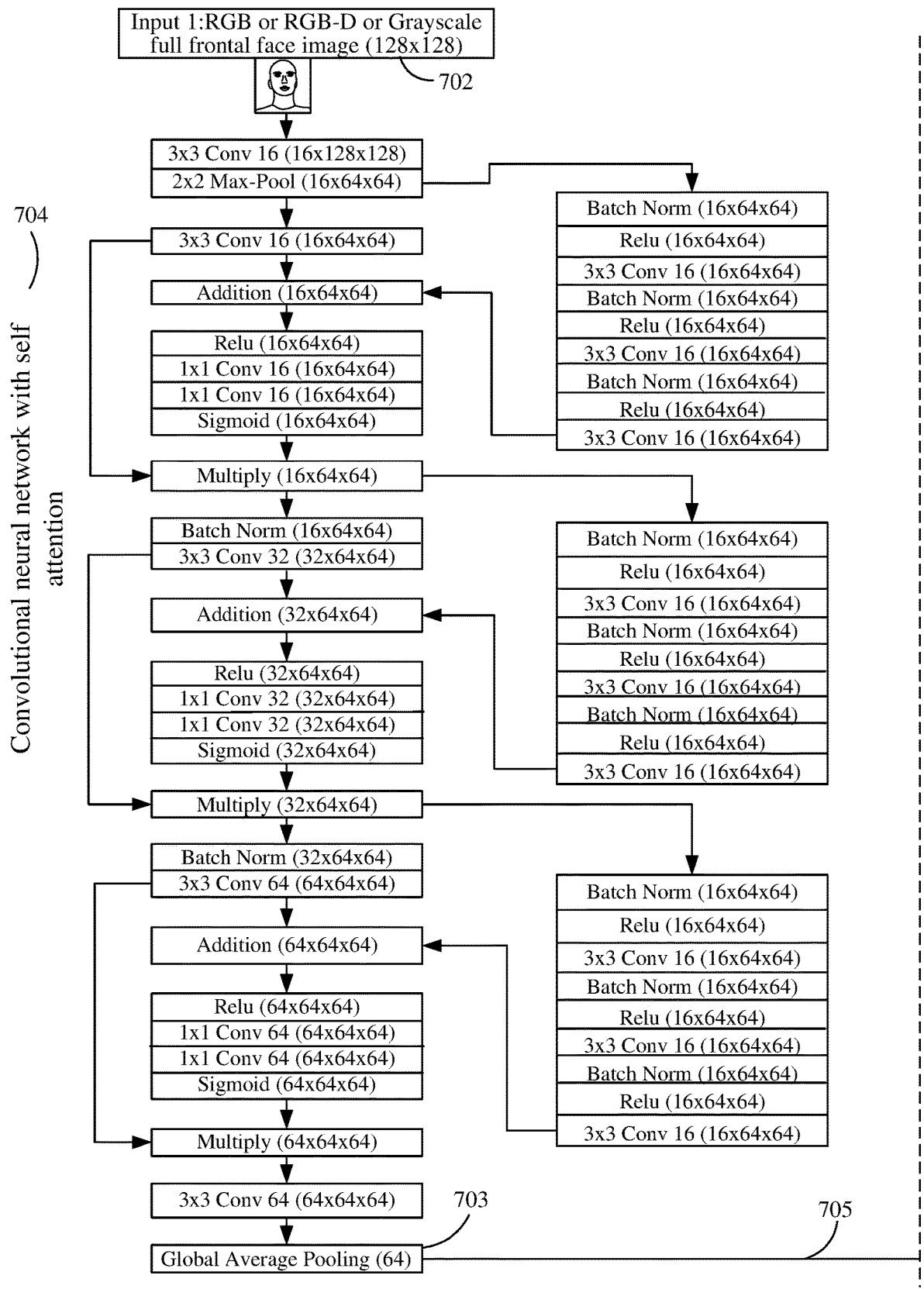
FIG. 7A and FIG. 7B show a detailed architecture of a body composition DLN for generating a prediction of the body composition of a user, in accordance with an exemplary embodiment of the present invention.
Figure 7B:
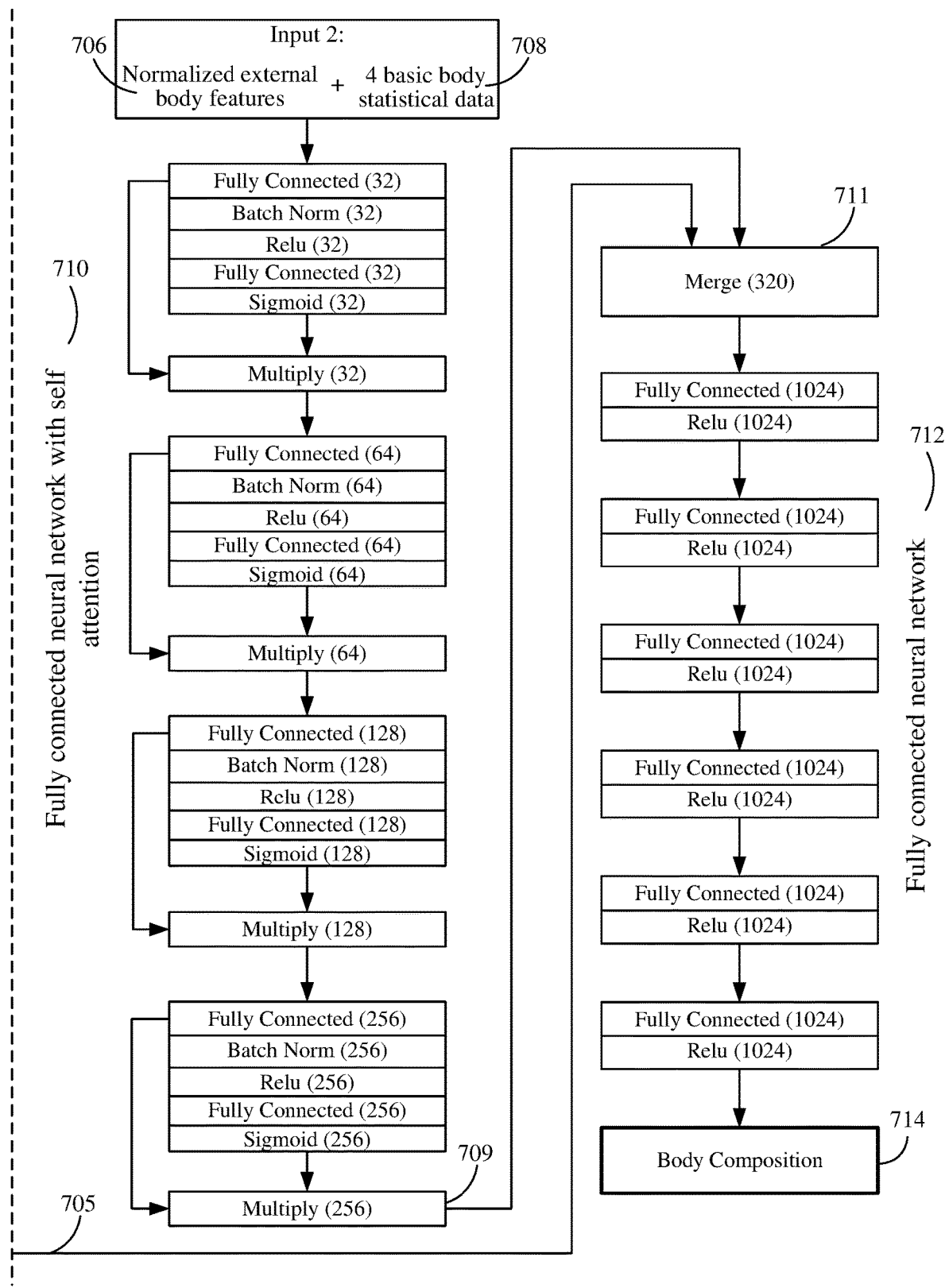

The processing module (104) transmits the body composition (120) to a display of the image capturing device (110). The body feature deep learning module, and the output deep learning module may be fully-connected neural networks, as shown in FIGS. 7A and 7B. However, the use of any other neural network, machine learning (ML), or artificial intelligence (AI) module to generate a body feature vector or a body composition is within the scope of the present invention.

The body composition (120) is any indicator of the internal components of the body of a living thing (e.g., human, animal). For example, the body composition (120) may be any indicator of muscle weight, bone weight, water content, and body fat of the user (116). FIG. 1 shows an illustrative example of a displayed body composition (120) indicating that the user (116) has 22% body fat, 30% muscle weight, 14% bone weight, and 58% water content. The body composition (120) may be selected from the group consisting of a Lean Body Mass (LBM), a Mass Body Fat (MBF), a Soft Lean Mass (SLM), and a Percent Body Fat (PBF).

Multiple types of body composition may be predicted by the systems and methods described herein. For example, estimating the skeletal muscle mass (i.e., lean mass without bone and visceral organ weight) is within the scope of the present invention. The estimation of any relative or absolute quantification of any type of muscle, bone, and/or organ within the body is within the scope of the present invention.

In one embodiment, from the one or more user parameters, a body mass index (BMI) may be calculated. The BMI may be used to calibrate the body measurement extraction using both the body weight and height. Additional user parameters may include at least one of race, country of origin, athleticism, and/or other demographic information associated with the user, among others. The height of the user may be used to normalize, or scale, front and/or side-view photos and provide a reference for a human in the image. In one embodiment, the other user parameters may also be obtained automatically from one or more third-party data sources, or from the server.

Some embodiments of the present invention leverage the AR (augmented reality) kit SDK (software development kit) provided in the image capturing device to measure the body composition of the user.

In one embodiment, three or more images of the user are utilized to measure body composition, including a front image, a side image, and an image taken at an approximately 45-degree angle. In some embodiment, a user video, for example, a front image, a 90, 180, or even 360-degree view of the user may be used. From the user video, one or more still frames or images, such as the front image, the side image, and/or a 45-degree view of the user may be extracted from the video. The system may automatically measure (e.g., using one or more AI algorithms) body composition using the images and the scale factor. In some embodiments, the user may indicate whether the user is dressed in tight, normal, or loose clothing for more accurate results. In other embodiments, the user may indicate whether the user is nude, dressed in undergarments, or fully clothed for more accurate results.

The terms "deep learning module" and "deep learning network (DLN)" are used interchangeably herein. The use of other neural network, machine learning (ML), or artificial intelligence (AI) modules to generate similar feature vectors and outputs as the deep learning modules and networks described herein is within the scope of the present invention.

FIG. 2 illustrates an example block diagram for predicting the body composition of a user through deep learning, in accordance with one embodiment of the present invention. The side image (212) and the front image (213) are received from the image capturing device (210) to identify and generate key points (234). One or more annotation key points (236) are generated from the side image (212) using a first key point deep learning network (DLN) or module (230), and one or more annotation keys points (238) are generated from the front image (213) using a second key point deep learning module (232). The first key point deep learning module (230) and the second key point deep learning module (232) have been trained on annotation key point training data, wherein the annotation key point training data includes one or more images for one or more sample users and a set of annotation key points for the one or more sample users. The one or more annotation key points (236) generated on the side image (212) and the one or more annotation key points (238) generated on the front image (213) are then used in an external body feature computation (240) step. The external body feature dimensions (242) are thus generated.

In embodiments where the received user images show a partially or fully clothed user, the key point DLN is trained to generate key points that determine the contour of body parts underneath user clothing. Exemplary embodiments of methods to generate external body feature dimensions (e.g., body part measurements) from user images by detecting key points, underneath user clothing, using one or more ML modules, are described in more detail in U.S. Pat. No. 10,321,728, which is hereby incorporated by reference in its entirety herein as if fully set forth herein.

In various embodiments, user parameters (250) are received. The user parameters (250) may include an age, a height, a weight, and a gender associated with the user (e.g., Age: 20 years, Gender: Male, Height: 70 inches, Weight: 160 pounds). In some embodiment, one or more user parameters are not received, but rather generated from the received user images. Exemplary embodiments of methods to generate body height from user images are described in more detail in U.S. Pat. No. 10,636,158, which is hereby incorporated by reference in its entirety herein as if fully set forth herein. Exemplary embodiments of methods to generate body weight from user images by detecting 2D key points using one or more ML modules are described in more detail in U.S. Pat. No. 10,962,404, which is hereby incorporated by reference in its entirety herein as if fully set forth herein.

In a scale factor computation step (252), the user parameter (250) (preferably the height of the user), the one or more annotation key points (236) generated on the side image (212), and the one or more annotation key points (238) generated on the front image (213), may be used for computation of a scale factor (254). Multiple methods for generating a scale factor are within the scope of the present invention, such as generating a scale factor based on a received real-world height of the user and a pixel height determined from annotation key points. A set of scaled external body feature dimensions (248) is thus computed through a normalization step (246), based on the scale factor (254) and the external body feature dimensions (242). The terms "scaling" and "normalization" are used interchangeably herein.

In a frontal face extraction step (220), the user's face may be extracted from the front image (213) of the user using a face extraction computer vision module to obtain a face image (222). The face extraction computer vision module has been trained on face training data that includes one or more front images for one or more sample users, the face images for the one or more sample users, or manually determined points or frames for extracting the face of the user. In an alternative embodiment shown by the dashed line (219), a face image (222), or a head image, is captured directly by the image capturing device or user device (210).

Finally, a prediction step (260) generates a prediction of internal body composition of the user (280) by (a) generating a face feature vector (272) from the face image (222) using a face image deep learning module (262), (b) generating a body feature vector (274) from the scaled external body feature dimensions (248) and the user parameters (250) using a body feature deep learning module (264), and (c) generating a prediction of the internal body composition (280) using an output deep learning module (266), based on the face feature vector (272) and the body feature vector (274). The internal body composition (280) is thus output to the image capturing device (210), as shown in FIG. 1.

In one embodiment, the three components of the internal body composition predictor (260), namely: the face image deep learning module (262), the body feature deep learning module (264), and the output deep learning module (266), were trained together, as a single DLN, on body composition data comprising face images, scaled external body feature dimensions, user parameters, and body compositions of a plurality of sample users.

In other embodiments, they were trained separately on body composition data comprising face images, scaled external body feature dimensions, user parameters, face feature vectors, body feature vectors, and body compositions of a plurality of sample users. For example, the output deep learning module (266) may have been trained separately on body composition data comprising face feature vectors, body feature vectors, and body compositions for one or more sample users. Similarly, the face image deep learning module (262) may have been trained on face feature training data where the face feature training data includes face images for one or more sample users and a set of face feature vectors for one or more sample users. The body feature deep learning module (264) may also have been trained on body feature training data where the body feature training data includes a set of scaled external body feature dimensions and one or more user parameters for one or more sample users.

In another embodiment, instead of using an image of the whole head or face (222) as an input to the internal body composition predictor (260), the head or face image (222) is subdivided into a plurality of subsections (e.g., quadrants, or any other partition of the face image). In this embodiment, instead of a single face image deep learning module (262), the internal body composition predictor (260) includes one or more face subsection deep learning networks (DLN) or modules. Each face subsection DLN receives a face subsection and generates a face subsection feature vector. The various face subsection feature vectors thus generated are concatenated to form the face feature vector (272). In this embodiment, the generation of the scaled external body feature dimensions (248) is optional. Hence, in one embodiment, external body feature computation (240) and scale factor computation (252) may not be required, and the body feature deep learning module (264) receives only the user parameters (250) as input.

In one exemplary embodiment, the scale factor is computed using one or more user parameters, such as the real height of the user, which is obtained and/or measured in order to perform a normalization or a scaling. In another embodiment, a weight may also be used in conjunction with the height. The height and weight of the user may be determined automatically (e.g., using computer vision algorithms or generated from one or more databases), or determined from the user (e.g., user input).

In one embodiment, the system may automatically generate (e.g., using one or more AI-algorithms) the internal body composition of the user using the front image, the side image, and the scale factor. In another embodiment, the user may indicate whether the user is dressed in tight, normal, or loose clothing for more accurate results.

In another exemplary embodiment, the scale factor is computed using a depth sensor or a Lidar. In another embodiment, the scale factor is computed from an object of known size captured on one of the images of the user. In yet another exemplary embodiment, the scale factor is determined based on distances between at least three feature points of a ground plane detected using an augmented reality software development kit (AR-SDK).

The Generation of Key Points, Feature Dimensions, and Face Images

Figure 3:
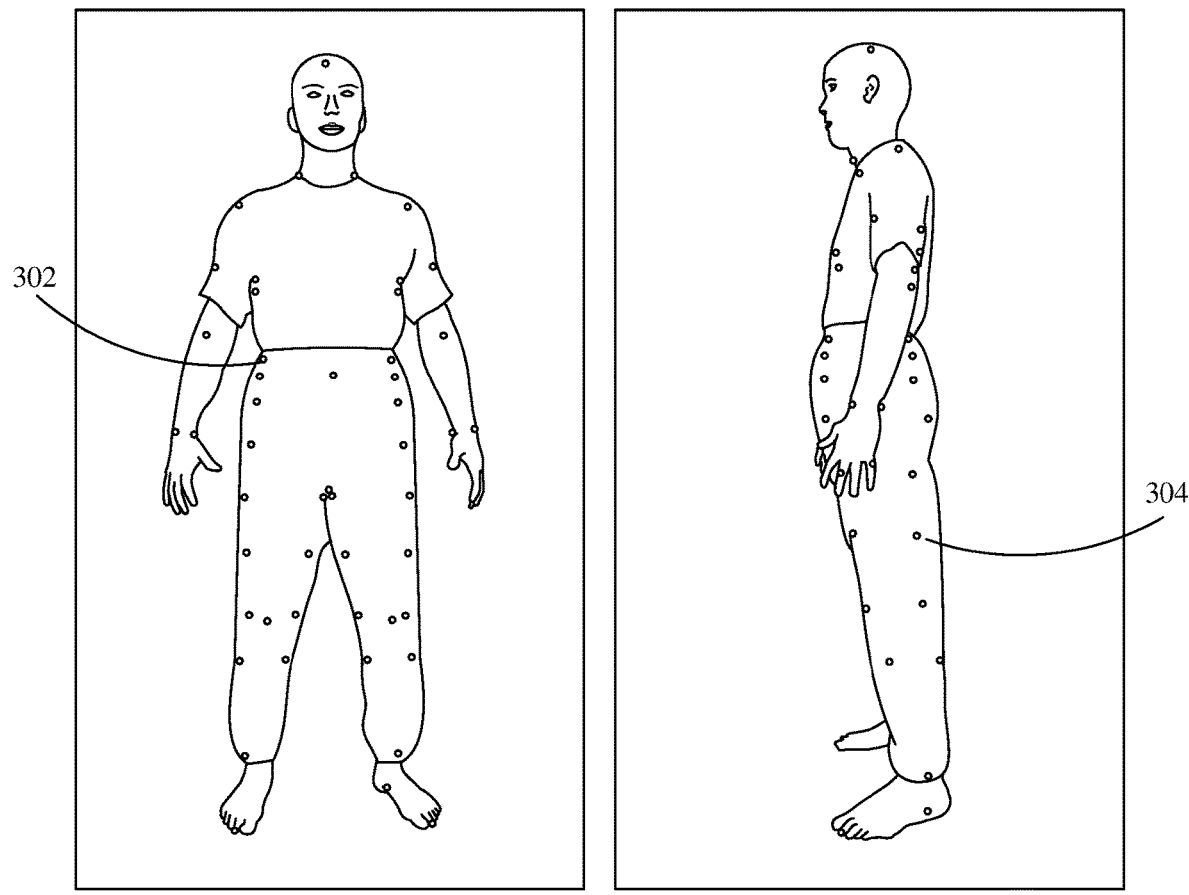
FIG. 3 shows an illustrative diagram of a front image (front view) and a side image (side view) showing generated key points, in accordance with an exemplary embodiment of the present invention.

FIG. 3 depicts an illustrative diagram of a front image (front view) and a side image (side view) showing generated key points, in accordance with an exemplary embodiment of the present invention. The system is configured to identify one or more key points (302, 304) for one or more body parts underneath a clothing of the user from the front image and the side image, using the key point deep-learning module. The one or more key points (302, 304) may be mapped to pixel points on the human body included in the image, and are used as a reference to compute one or more external body feature dimensions of the user. The key point deep learning module has been trained on key point training data including one or more front images and side images for one or more sample users, and one or more predicted (training) key points on each of the one or more front images and side images to generate external body features for the one or more sample users. The training key points may be manually determined by annotators or automatically generated by key point annotation software for key point DLN training purposes. In one embodiment, the key point deep learning module has been trained on one or more images for sample users in different poses and different clothing, with an annotation line or a set of key points for each body feature, for the one or more sample users. The annotation lines may be drawn manually or generated automatically on the images of the sample user.

The predicted key points may refer to body, hand, foot, or facial key points on the user image(s). A human body shown in the user image(s) includes a plurality of features that may be utilized as body key points, including, without limitation, the left eye, the right eye, the left ear, the right ear, the nose, the neck, the left shoulder, the right shoulder, the left elbow, the right elbow, the left wrist, the right wrist, the left hip, the right hip, the left knee, the right knee, the left ankle, and the right ankle. In one embodiment, the key point may be estimated from a user's pose on the user image.

In one embodiment, a key point DLN (230 or 232) generates annotation lines linking key points on each body feature and corresponding to a given body feature measurement. The system may then generate the external body feature dimensions (242) utilizing the annotation lines on relevant body features (see FIG. 4). In another embodiment, annotation lines are generated at the external body feature computation (240) step.

Figure 4:
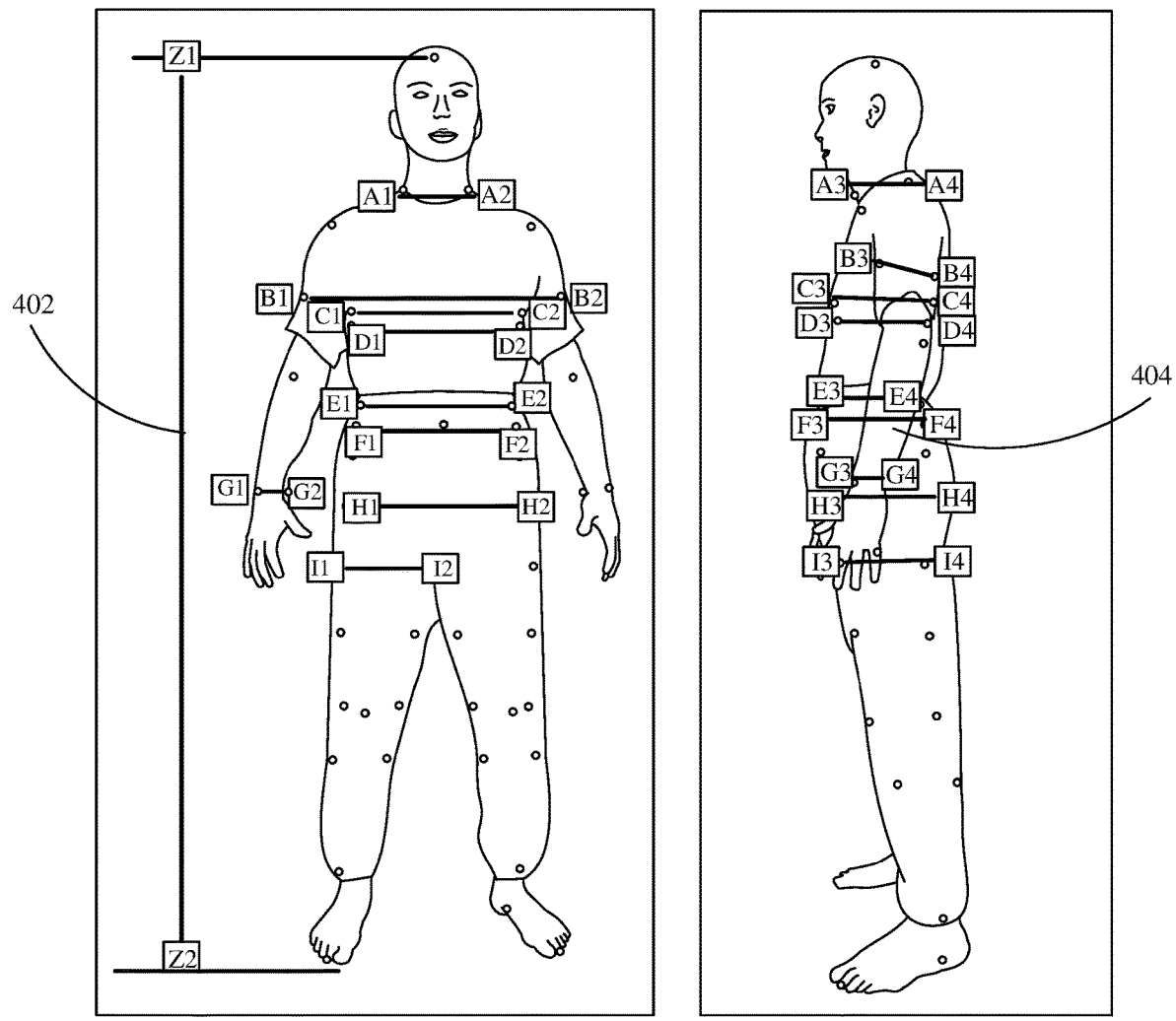
FIG. 4 shows an illustrative diagram of a front image (front view) and a side image (side view) showing annotated key points and the computation of external body feature dimensions, in accordance with an exemplary embodiment of the present invention.

FIG. 4 shows an illustrative diagram of a front image (front view) and a side image (side view) showing annotated key points and the computation of external body feature dimensions, in accordance with an exemplary embodiment of the present invention. The annotation key points generated on the front and side images are used to compute one or more external body feature dimensions. As mentioned above, a computer vision module may generate annotation lines (402 or 404) connecting two or more key points on the human body to determine external body feature dimensions for each body feature.

For example, referring to FIG. 4, the key point deep learning module (230 or 232) or the external body feature computation module (240) may draw a full-body annotation line indicating the user's height, with a pixel dot (Z2) representing the bottom of the user's feet and another pixel dot (Z1) representing the top of the user's head. Similarly, for the bicep width or circumference, the system may draw a line perpendicular to the skeletal line at the bicep location; for the chest, the system may connect two chest dots instead. From the annotation of each body feature, a scaled external body feature dimension (248) may then be obtained by normalizing (246) the external dimension of the user's body feature (e.g., height, biceps, chest).

The annotation line (402, 404) is a reference length defined by a distance between the pixel location of one or more key points (for example, a height of the user is computed as distance between the pixel Z1 and Z2, denoted "Z1_Z2"). The one or more external body feature dimensions may be selected from the group consisting of a height, a belly depth, a belly length, a belly waist, a bust girth, a hip girth, a neck girth, a thigh girth, an under bust girth, an upper arm girth, a waist girth, and a wrist girth, associated with the user. In one embodiment, and in reference to FIG. 4, the one or more external body feature dimensions are computed as follows: Height_pxl: Z1_Z2, Belly_depth_pxl: F3_F4, Belly_length_pxl: F1_F2, Belly_waist_pxl: 2×(F1_F2)+2×(F3_F4), Bust_girth_pxl: 2×(C1_C2)+2×(C3_C4), Hip_girth_pxl: 2×(H1_H2)+2×(H3_H4), Neck_girth_pxl: 2×(A1_A2)+2×(A3_A4), Thigh_girth_pxl: 2×(I1_I2)+2×(I3_I4), Under_Bust_girth_pxl: 2×(D1_D2)+2×(D3_D4), Upper_arm_girth_pxl: 2×(B1_B2)+2×(B3_B4), Waist_girth_pxl: 2×(E1_E2)+2×(E3_E4) and Wrist_girth_pxl: 2×(G1_G2)+2×(G3_G4).

In one exemplary embodiment, computing the set of one or more external body feature dimensions of the user based on the generated annotation key points includes using at least one annotated image to calculate: (a) a circumference of an annotated body part; (b) a body part image area of an annotated body part; or (c) a body part volume of an annotated body part.

In another exemplary embodiment, the scale factor (i.e., normalization factor) is derived by obtaining a real height of the user and the height generated from the annotation key points (e.g., Height_pxl: Z1_Z2), where the scale factor is the real height divided by the pixel height. In yet another exemplary embodiment, the pixel height of the user in the front image is detected and used along with the real height to normalize all annotation line measurements.

In one exemplary embodiment, the system is configured to compute the set of one or more scaled external body feature dimensions of the user based on the set of one or more external body feature dimensions and the scale factor. In the illustrative example above, the set of one or more scaled external body feature dimensions are
Belly_depth=Belly_depth_pxl×scale factor,
Belly_length=Belly_length_pxl×scale factor,
Belly_waist=Belly_waist_pxl×scale factor,
Bust_girth=Bust_girth_pxl×scale factor,
Hip_girth=Hip_girth_pxl×scale factor,
Neck_girth=Neck_girth_pxl×scale factor,
Thigh_girth=Thigh_girth_pxl×scale factor,
Under_Bust_girth=Under_Bust_girth_pxl×scale factor,
Upper_arm_girth=Upper_arm_girth_pxl×scale factor,
Waist_girth=Waist_girth_pxl×scale factor, and
Wrist_girth=Wrist_girth_pxl×scale factor.

Figure 5:
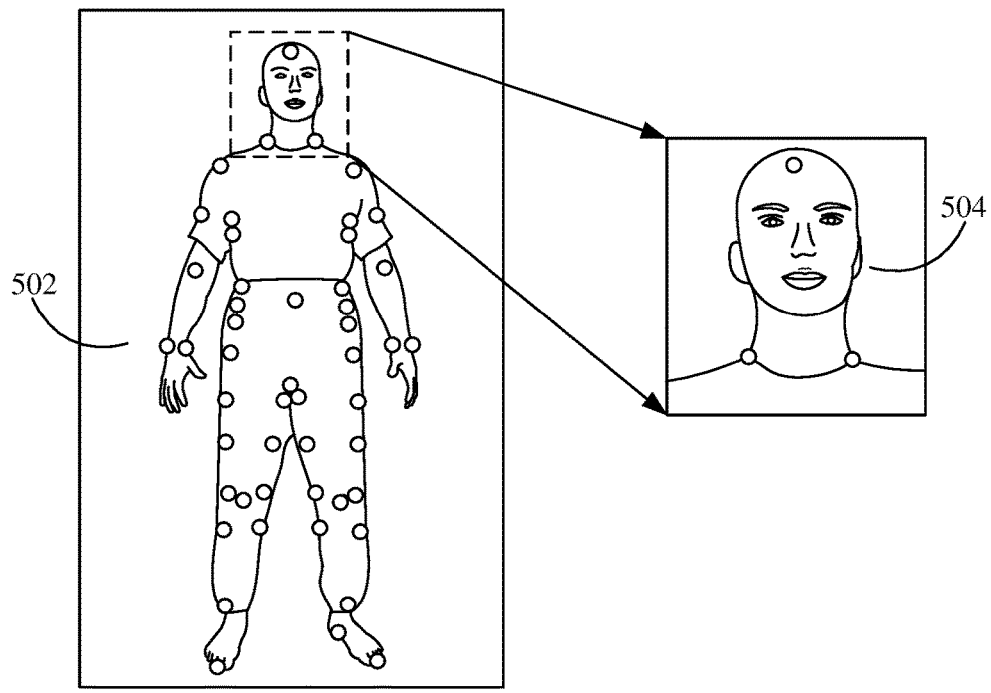
FIG. 5 illustrates the process of frontal face extraction from a front image of a user, in accordance with an exemplary embodiment of the present invention.

FIG. 5 illustrates the process of frontal face extraction from a front image of a user, in accordance with an exemplary embodiment of the present invention. In one embodiment, a part of a user image (502) that includes the complete frontal face (504) is clipped, as illustrated in FIG. 5. In one embodiment, the system is configured to extract the user's face image (504) from the front image (502) of the user using a face extraction computer vision module or a face extraction deep learning module. In one example embodiment, the user's face image (504) is extracted using the dlib open source library. In other embodiments, other face detection and object detection computer vision and deep-learning based schemes can be used, such as single shot detector (SSD). Similar processes may be used for the detection of a head image, a face image subsection, or a head image subsection from a user image.

Deep Learning Network Architecture and Performance

Figure 6:
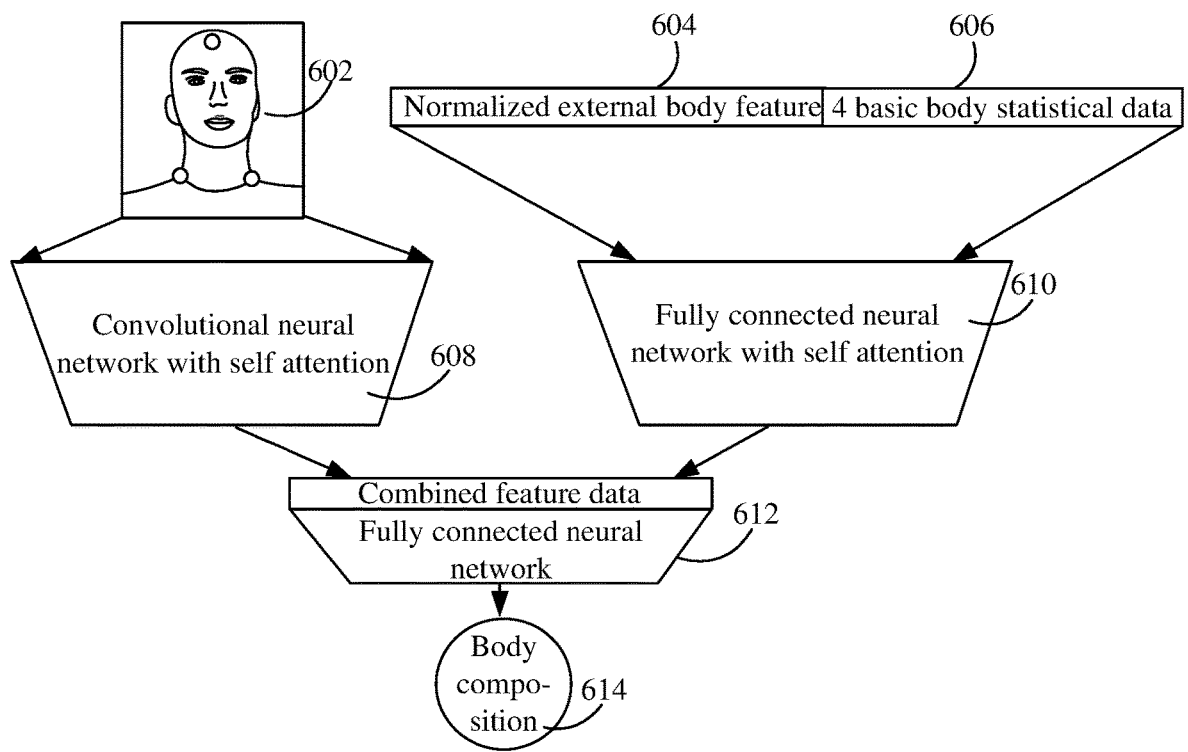
FIG. 6 shows an illustrative diagram of a body composition deep learning network (DLN) for generating a prediction of the body composition of a user, in accordance with an exemplary embodiment of the present invention.

FIG. 6 shows an illustrative diagram of a body composition deep learning network (DLN), or internal body composition predictor (260) module, for generating a prediction of the body composition of a user, in accordance with an exemplary embodiment of the present invention. The multimodal body composition DLN of FIG. 6 has two input branches: a face image deep learning module (608) and a body feature deep learning module (610), both passing their outputs to an output deep learning module (612). The body composition DLN outputs body composition as a regression task.

The face image deep learning module (608) is configured for receiving a user's face image (602) and generating a face feature vector. The body feature deep learning module (610) is configured for receiving one or more user parameters (606) and a set of one or more scaled external body feature dimensions (604) for generating a body feature vector. The output deep learning module (612) is configured for receiving the face feature vector from the face image deep learning module (608) and the body feature vector from the body feature deep learning module (610) to generate the body composition (614) of the user. The body composition (614) is any indicator of the physical composition of a body, such as the muscle weight, the bone weight, the water content, or the body fat of the user. The face image deep learning module (608) may be implemented as a Convolutional Neural Network (CNN), and the body feature deep learning module (610) and the output deep learning module (612) may be implemented as fully-connected neural networks. However, the use of any other neural network, machine learning (ML), or artificial intelligence (AI) module to generate a face feature vector, a body feature vector, or a body composition is within the scope of the present invention.

In one embodiment, the three components of the body composition deep learning module of FIG. 6, namely: the face image deep learning module (608), the body feature deep learning module (610), and the output deep learning module (612), are trained together, as a single DLN, on body composition data comprising face images, scaled external body feature dimensions, user parameters, and body compositions of a plurality of sample users. In other embodiments, they are trained separately on body composition data comprising face images, scaled external body feature dimensions, user parameters, face feature vectors, body feature vectors, and body compositions of a plurality of sample users, before being combined.

In the embodiment of FIG. 6, the face image deep learning module (608) and the body feature deep learning module (610) are neural networks that use self-attention, a set of architectural attributes allowing them to assign weights to inputs of various layers through, for example, feed forward structures and multiplication layers (see FIGS. 7A and 7B). The use of self-attention architectures allows a neural network to assign value to certain inputs at the expense of others, thus providing added accuracy to the output body composition.

In one embodiment, the body composition (614) is selected from the group consisting of the Lean Body Mass (LBM), the Mass Body Fat (MBF), the Soft Lean Mass (SLM), and the Percent Body Fat (PBF).

In one embodiment, instead of using an image of the whole face (602) as an input to the body composition deep learning module in FIG. 6, the face image (602) is subdivided into a plurality of subsections (e.g., quadrants, or any other partition of the face image). In this embodiment, instead of a single face image deep learning module (608), the body composition deep learning module (FIG. 6) includes one or more face subsection deep learning networks (DLN) or modules. Each face subsection DLN receives a face subsection and generates a face subsection feature vector. The various face subsection feature vectors thus generated are concatenated with the output of the body feature deep learning module (610) to form the input of the output deep learning module (612). In this embodiment, the generation of the set of one or more scaled external body feature dimensions (604) is optional. Hence, in one embodiment, external body feature computation (240) and scale factor computation (252) are absent, and the body feature deep learning module (610) receives only the user parameters (606) as input.

Furthermore, in one embodiment of the present invention, the user images (212 and/or 213) are used to extract one or more head images or head subsections (e.g., 222) which are fed into one or more head feature or head subsection DLNs (e.g., 262) to generate one or more head feature or head subsection vectors (e.g., 272). In this embodiment, the body feature deep learning module (264, 610) receives only the user parameters (250, 606) as input, and the key point DLN(s) (230 and 232), external body feature computation step (240), and scale factor computation step (252) are absent.

FIG. 7A and FIG. 7B show a detailed architecture of a body composition DLN for generating a prediction of the body composition of a user, in accordance with an exemplary embodiment of the present invention. Specifically, FIG. 7A and FIG. 7B show an illustrative architecture of the body composition DLN of FIG. 6 for generating the prediction of the body composition of the user (614), in accordance with an exemplary embodiment of the present invention. FIG. 7A and FIG. 7B show illustrative architectures for the three components of the body composition deep learning module of FIG. 6, namely: the face image deep learning module (608), the body feature deep learning module (610), and the output deep learning module (612). FIG. 7A shows one embodiment of the face image deep learning module (608) as a convolutional neural network (CNN) with self-attention (704). The input of the face image CNN (704) is labeled as Input 1 (702) and consists of a square frontal face image. Various image formats are within the scope of the present invention, including but not limited to red green blue (RGB), red green blue depth (RGB-D), and Grayscale images. The output (705) of the face image CNN (704) is the face feature vector (272).

FIG. 7B shows one embodiment of the body feature deep learning module (610) as a fully connected neural network with self-attention (710). In this embodiment, the input of the body feature DLN (710) is labeled Input 2 and consists of the concatenation of the scaled external body feature dimensions (248), here labeled "normalized external body features" (706), combined with the input user parameters (250), here labeled "4 basic body statistical data" (708). The inputs of the body feature DLN (710) are combined into a single array. In one embodiment, each of the two inputs are encoded into a 16-element array and concatenated into a single 32-element array. The output of the last layer (709) of the body feature DLN (710) is the body feature vector (274).

FIG. 7B also shows one embodiment of the output deep learning module (612) as a fully connected neural network (712). The output deep learning module (e.g., DLN) (712) merges the body feature vector generated by the last layer (709) of the body feature DLN (710) with the face feature vector (705) generated by the face image CNN (710), yielding the body composition (714).

In the exemplary embodiment of FIGS. 7A and 7B, the size and dimensions of each layer's output arrays, matrices, and tensors, are indicated in parentheses. For example, while the input of the face image CNN (704) is a 128×128 image, the size of the face feature vector (705) that is generated by the last pooling layer (703) of the face image CNN (704) is 64.

The neural network architectures illustrated in FIGS. 7A and 7B use convolutional ("Conv") layers, max/average pooling layers, batch normalization ("Batch Norm") layers, Rectified Linear Unit ("Relu") layers, addition layers, multiplication ("Multiply") layers, Sigmoid layers, fully connected layers, and merging layers. In FIGS. 7A and 7B, multiplication and addition are element-by-element multiplication and summation, both operations producing tensors or matrices of the same dimensions as the inputs. In addition, the term "merging" in FIGS. 7A and 7B represents vector concatenation.

In the embodiment of FIGS. 7A and 7B, the face image CNN (704) and the body feature DLN (710) are neural networks that use self-attention, a set of architectural attributes allowing them to assign weights to inputs of various layers through, for example, feed forward structures and multiplication layers, thus providing added accuracy to the output body composition.

The DLN architectures and algorithms listed above for the various deep learning networks and modules disclosed herein are only illustrative algorithms that are within the scope of the present invention, and the present invention is not limited to the use of the listed DLN algorithms. Other DLN algorithms are also within the scope of the present invention. Moreover, other machine learning (ML) methods may be used instead of or in combination with the various listed DLN architectures and algorithms. Other ML algorithms including, but not limited to, regressors, nearest neighbor algorithms, decision trees, support vector machines (SVM), Adaboost, Bayesian networks, fuzzy logic models, evolutionary algorithms, and so forth, are hence within the scope of the present invention.

Figure 8:
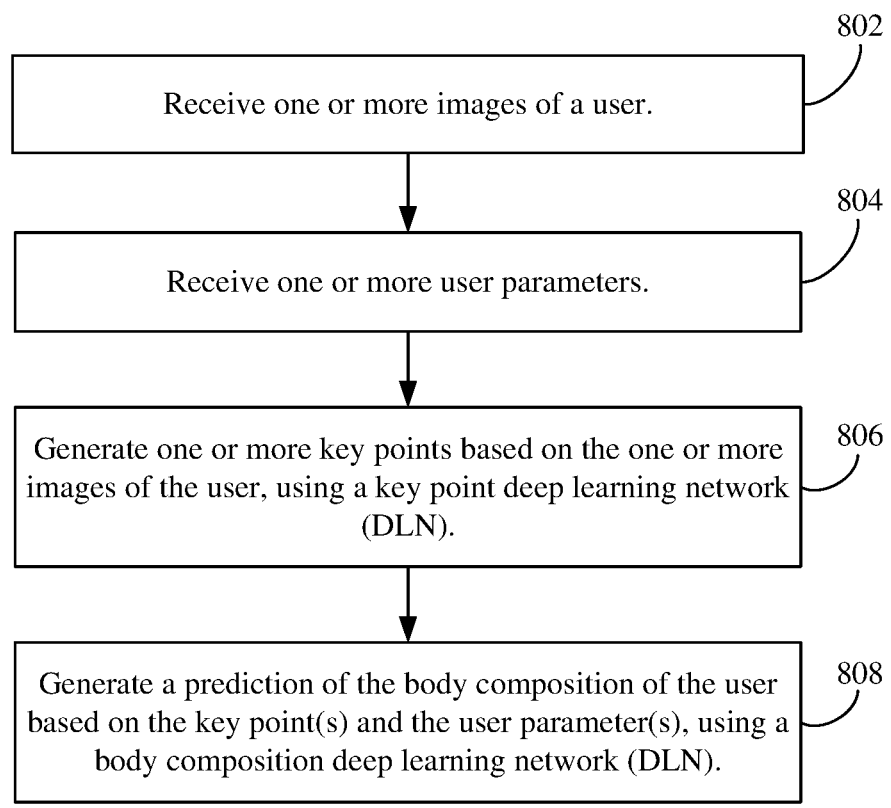
FIG. 8 shows an example flow chart for a method for predicting the body composition of a user, in accordance with one embodiment of the present invention.

FIG. 8 shows an example flow chart for a method for predicting the body composition of a user, in accordance with one embodiment of the present invention. At step 802, one or more images are received. These images may include front or side images of the user with or without clothing. In various embodiments, the input user images show the full body of the user. In other embodiments, the input user images are partial images of the user showing one or more body parts of the user rather than the full image. At step 804, one or more user parameters, such as age, gender, ethnicity, weight, or height, are received. At step 806, one or more key points are generated based on the received user image(s), using a key point deep learning network (DLN). At step 808, a prediction of the body composition of the user is generated based on the key point(s) and the user parameter(s), using a body composition deep learning network (DLN).

FIG. 9 is a table showing the performance of one embodiment of a body composition DLN that uses the illustrative body composition prediction architecture of FIGS. 7A and 7B in generating the Soft Lean Mass (SLM) and Percent Body Fat (PBF) of a user. SLM is a body composition measure of the mass, in kilograms (KG), of body water, protein, and non-skeletal minerals. PBF is a body composition measure of the mass percentage (%) of fat. The two left columns of FIG. 9 show the actual SLM and PBF of various sample users, while the two right columns show the SLM and PBF measures as predicted by the body composition DLN embodiment of FIGS. 7A and 7B. The actual and predicted SLM and PBF measures are compared statistically in FIGS. 10 and 11 below.

Figure 10:
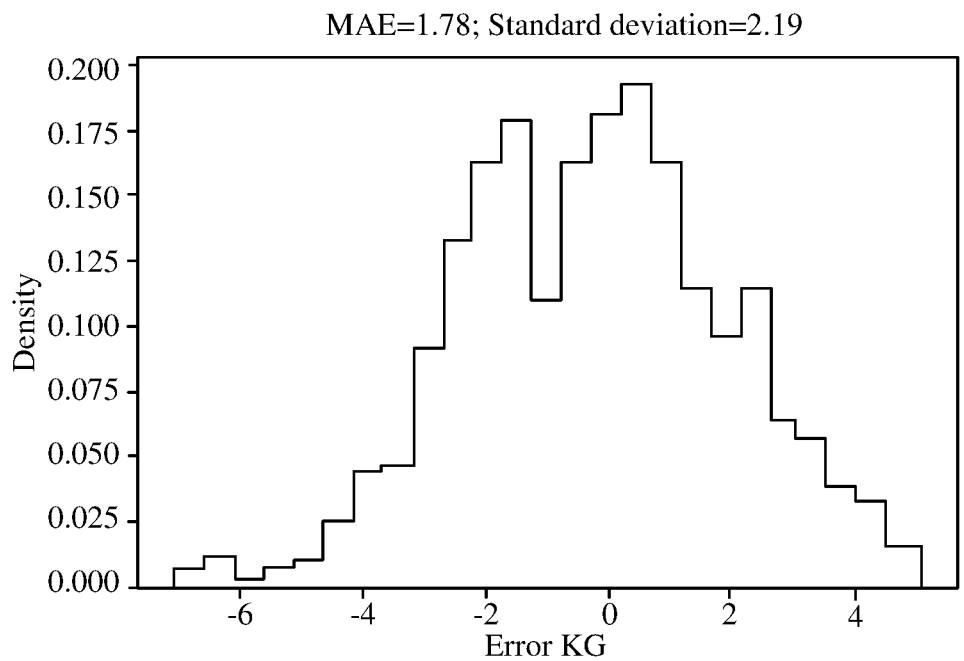
FIG. 10 shows a density distribution depicting the accuracy of one embodiment of a body composition DLN that uses the illustrative body composition prediction architecture of FIGS. 7A and 7B in generating the SLM of a user.

FIG. 10 shows a density distribution depicting the accuracy of one embodiment of a body composition DLN that uses the illustrative body composition prediction architecture of FIGS. 7A and 7B in generating the SLM of a user. Specifically, FIG. 10 shows the density distribution of the SLM error (i.e., the difference between the actual and predicted SLM for each of the sample users) based on the results of FIG. 9. FIG. 10 shows a mean absolute error (MAE) of 1.78 KG and a standard deviation of 2.19 KG.

Figure 11:
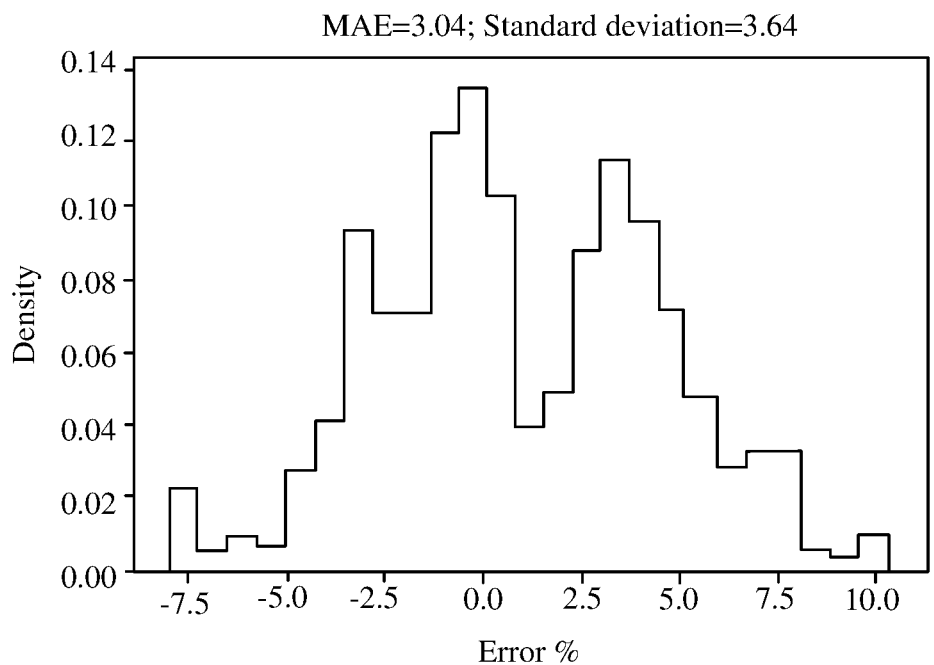
FIG. 11 shows a density distribution depicting the accuracy of one embodiment of a body composition DLN that uses the illustrative body composition prediction architecture of FIGS. 7A and 7B in generating the PBF of a user.

FIG. 11 shows a density distribution depicting the accuracy of one embodiment of a body composition DLN that uses the illustrative body composition prediction architecture of FIGS. 7A and 7B in generating the PBF of a user. Specifically, FIG. 11 shows the density distribution of the PBF error (i.e., the difference between the actual and predicted PBF for each of the sample users) based on the results of FIG. 9. FIG. 11 shows a mean absolute error (MAE) of 3.04% and a standard deviation of 3.64%.

Both error density distributions of FIGS. 10 and 11 peak at zero, showing an accurate body composition for the largest subset of sample users. The performance results of FIGS. 9, 10, and 11 are subject to improvement based on numerous factors including neural network and ML architectures, training data, and training processes used for the body composition DLN and/or its various components.

Illustrative Embodiments

In one exemplary embodiment, a method for measuring the body composition of a user is provided. The method comprising receiving a front image and a side image of the user, and one or more user parameters, generating a prediction of the body composition of the user based on the front image and the side image of the user, and the one or more user parameters, using a body composition deep learning module and transmitting the body composition to a display of an image capturing device.

In another exemplary embodiment, generating the prediction of the body composition using the body composition deep learning module is further based on a user' face image. In one embodiment, generation of the prediction of the body composition using the body composition deep learning module is further based on a set of one or more scaled external body feature dimensions.

In one exemplary embodiment, the method is configured for generating the height and the weight of the user from one or more user images. The one or more user images are selected from the group consisting of the front image and the side image of the user.

In another exemplary embodiment, the method is configured for generating a set of one or more external body feature dimensions for computing the set of one or more scaled external body feature dimensions. The set of one or more external body feature dimensions is extracted from the front image and the side image of the user using one or more annotation key points. The one or more annotation key points are generated using a key point deep-learning module. The set of one or more scaled external body feature dimensions are computed from the set of one or more external body feature dimensions using a scale factor. The scale factor is computed using one of a depth sensor and a Lidar.

In one exemplary embodiment, a system for predicting the body composition of a user is disclosed, the system comprising an image capturing device and a server. The image capturing device is configured to capture a front image and a side image of the user and receive one or more user parameters. The server includes an input module and a processing module. The input module is configured to receive the front image and the side image of the user, and the one or more user parameters, through a wireless network from the image capturing device. The processing module is configured to execute instructions to identify one or more annotation key points for one or more body parts underneath a clothing of the user from the front image and the side image using a key point DLN, compute a set of one or more external body feature dimensions of the user based on the one or more annotation key points, derive a scale factor based on the one or more user parameters and the one or more annotation key points, compute a set of one or more scaled external body feature dimensions of the user based on the set of one or more external body feature dimensions and the scale factor, and extract a user's face image from the front image of the user using a face extraction computer vision module. The processing module is further configured to trigger a face image DLN to receive the user's face image and generate a user's face feature vector from the user's face image. Further, the processing module is configured to trigger a body feature DLN to receive the set of one or more scaled external body feature dimensions of the user and the one or more user parameters and generate a user's body feature vector from the set of one or more scaled external body feature dimensions of the user and the one or more user parameters. Further, the processing module is configured to trigger an output DLN to receive the user's face feature vector from the face image DLN and the user's body feature vector from the body feature DLN, generate a prediction of the body composition of the user based on the user's face feature vector and the user's body feature vector, and transmit the body composition to a display of the image capturing device.

In another exemplary embodiment, the computing of the set of one or more external body feature dimensions of the user based on the one or more annotation key points includes at least one step selected from the group consisting of (a) calculating at least one circumference of at least one annotated body part using an annotated front image and an annotated side image; (b) calculating at least one body part image area of at least one annotated body part using an annotated front image and an annotated side image; and (c) calculating at least one body part volume of at least one annotated body part using an annotated front image and an annotated side image.

Exemplary System Architecture

An exemplary embodiment of the present disclosure may include one or more servers (management computing entities), one or more networks, and one or more clients (user computing entities). Each of these components, entities, devices, and systems (similar terms used herein interchangeably) may be in direct or indirect communication with, for example, one another over the same or different wired or wireless networks. Additionally, while FIGS. 12 and 13 illustrate the various system entities as separate, standalone entities, the various embodiments are not limited to this particular architecture.

Exemplary Management Computing Entity

Figure 12:
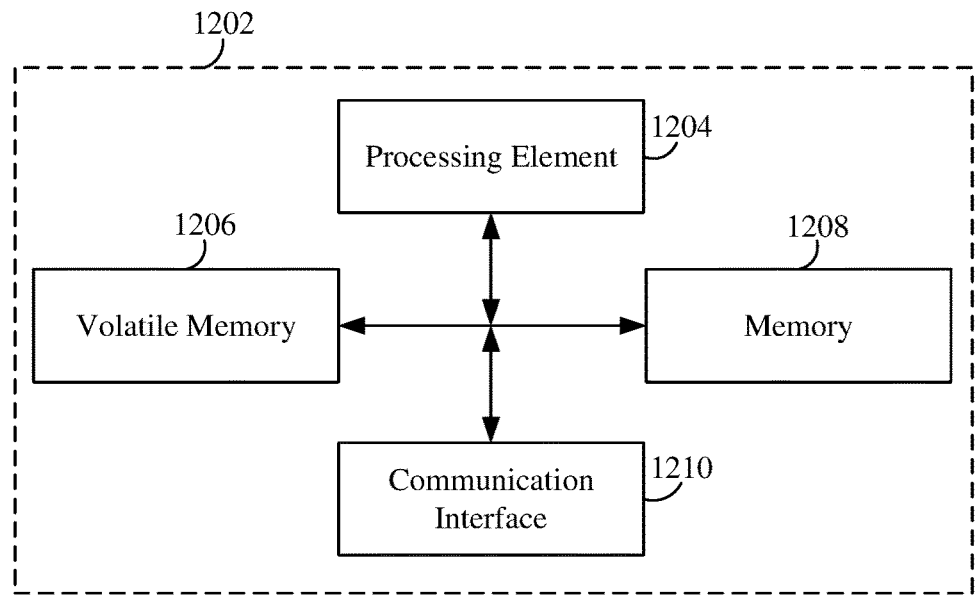
FIG. 12 provides a schematic view of a server (management computing entity) that can be used for predicting a user's body composition, in conjunction with embodiments of the present invention.
Figure 13:
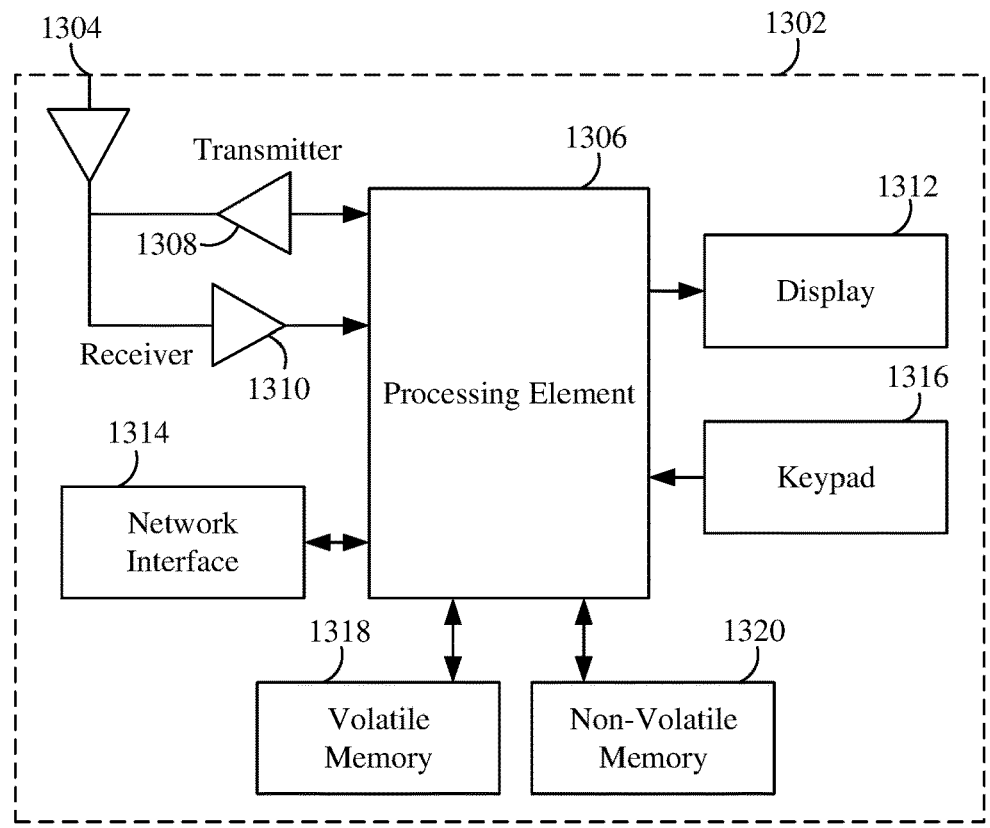
FIG. 13 provides an illustrative schematic representative of a client (user computing entity) that can be used for predicting a user's body composition, in conjunction with embodiments of the present invention.

FIG. 12 provides a schematic view of a server (management computing entity) (1202) that can be used in conjunction with embodiments of the present disclosure. In general, the terms computing entity, computer, entity, device, system, and/or similar words used herein interchangeably may refer to, for example, one or more computers, computing entities, desktop computers, mobile phones, tablets, phablets, notebooks, laptops, distributed systems, gaming consoles, watches, glasses, iBeacons, proximity beacons, key fobs, radio frequency identification (RFID) tags, earpieces, scanners, televisions, dongles, cameras, wristbands, wearable items/devices, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, and/or comparing (similar terms used herein interchangeably). In one embodiment, these functions, operations, and/or processes can be performed on data, content, and/or information (similar terms used herein interchangeably).

As indicated, in one embodiment, the management computing entity (1202) may also include one or more communications interfaces (1210) for communicating with various computing entities, such as by communicating data, content, and/or information (similar terms used herein interchangeably) that can be transmitted, received, operated on, processed, displayed, stored, and/or the like.

As shown in FIG. 12, in one embodiment, the management computing entity (1202) may include or be in communication with one or more processing elements (1204) (also referred to as processors and/or processing circuitry—similar terms used herein interchangeably) that communicate with other elements within the management computing entity (1202) via a bus, for example. As will be understood, the processing element (1204) may be embodied in a number of different ways. For example, the processing element (1204) may be embodied as one or more complex programmable logic devices (CPLDs), microprocessors, multi-core processors, coprocessing entities, application-specific instruction-set processors (ASIPs), microcontrollers, and/or controllers. Further, the processing element (1204) may be embodied as one or more other processing devices or circuitry. The term circuitry may refer to an entire hardware embodiment or a combination of hardware and computer program products. Thus, the processing element (1204) may be embodied as integrated circuits, application-specific integrated circuits (ASICs), field-programmable gate arrays (FPGAs), programmable logic arrays (PLAs), hardware accelerators, other circuitry, and/or the like. As will therefore be understood, the processing element (1204) may be configured for a particular use or configured to execute instructions stored in volatile or non-volatile media or otherwise accessible to the processing element (1204). As such, whether configured by hardware or computer program products, or by a combination thereof, the processing element (1204) may be capable of performing steps or operations according to embodiments of the present disclosure when configured accordingly.

In one embodiment, the management computing entity (1202) may further include or be in communication with non-volatile media (also referred to as non-volatile storage, memory, memory storage, and/or memory circuitry—similar terms used herein interchangeably). In one embodiment, the non-volatile storage or memory may include one or more non-volatile storage or memory media (1208), including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, and/or database management system (similar terms used herein interchangeably) may refer to a collection of records or data that is stored in a computer-readable storage medium using one or more database models, such as a hierarchical database model, network model, relational model, entity-relationship model, object model, document model, semantic model, graph model, and/or the like.

In one embodiment, the management computing entity (1202) may further include or be in communication with volatile media (also referred to as volatile storage, memory, memory storage, memory and/or circuitry—similar terms used herein interchangeably). In one embodiment, the volatile storage or memory may also include one or more volatile storage or memory media (1206), including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element (1204). Thus, the databases, database instances, database management systems, data, applications, programs, program modules, scripts, source code, object code, byte code, compiled code, interpreted code, machine code, executable instructions, and/or the like may be used to control certain aspects of the operation of the management computing entity (1202) with the assistance of the processing element (1204) and operating system.

As indicated, in one embodiment, the management computing entity (1202) may also include one or more communications interfaces (1210) for communicating with various computing entities, such as by communicating data, content, and/or information (similar terms used herein interchangeably) that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the management computing entity (1202) may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High-Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the management computing entity (1202) may include or be in communication with one or more input elements, such as a keyboard input, a mouse input, a touch screen/display input, motion input, movement input, audio input, pointing device input, joystick input, keypad input, and/or the like. The management computing entity (1202) may also include or be in communication with one or more output elements (not shown), such as audio output, video output, screen/display output, motion output, movement output, and/or the like.

As will be appreciated, one or more of the components of the management computing entity (1202) may be located remotely from other management computing entity (1202) components, such as in a distributed system. Furthermore, one or more of the components may be combined and additional components performing functions described herein may be included in the management computing entity (1202). Thus, the management computing entity (1202) can be adapted to accommodate a variety of needs and circumstances. As will be recognized, these architectures and descriptions are provided for exemplary purposes only and are not limiting to the various embodiments.

Exemplary User Computing Entity

A user may be an individual, a company, an organization, an entity, a department within an organization, a representative of an organization and/or person, and/or the like.

FIG. 13 provides an illustrative schematic representative of a client (user computing entity) (1302) that can be used in conjunction with embodiments of the present disclosure. In general, the terms device, system, computing entity, entity, and/or similar words used herein interchangeably may refer to, for example, one or more computers, computing entities, desktops, mobile phones, tablets, phablets, notebooks, laptops, distributed systems, gaming consoles, watches, glasses, key fobs, radio frequency identification (RFID) tags, earpieces, scanners, cameras, wristbands, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. User computing entities (1302) can be operated by various parties. As shown in FIG. 13, the user computing entity (1302) can include an antenna (1304), a transmitter (1308) (e.g., radio), a receiver (1310) (e.g., radio), and a processing element (1306) (e.g., CPLDs, microprocessors, multi-core processors, coprocessing entities, ASIPs, microcontrollers, and/or controllers) that provides signals to and receives signals from the transmitter (1308) and receiver (1310), respectively.

The signals provided to and received from the transmitter (1308) and the receiver (1310), respectively, may include signaling information in accordance with air interface standards of applicable wireless systems. In this regard, the user computing entity (1302) may be capable of operating with one or more air interface standards, communication protocols, modulation types, and access types. More particularly, the user computing entity (1302) may operate in accordance with any of a number of wireless communication standards and protocols, such as those described above with regard to the management computing entity (1202). In a particular embodiment, the user computing entity (1302) may operate in accordance with multiple wireless communication standards and protocols, such as UMTS, CDMA2000, 1×RTT, WCDMA, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the user computing entity (1302) may operate in accordance with multiple wired communication standards and protocols, such as those described above with regard to the management computing entity (1202) via a network interface (1314).

Via these communication standards and protocols, the user computing entity (1302) can communicate with various other entities using concepts such as Unstructured Supplementary Service Data (US SD), Short Message Service (SMS), Multimedia Messaging Service (MMS), Dual-Tone Multi-Frequency Signaling (DTMF), and/or Subscriber Identity Module Dialer (SIM dialer). The user computing entity (1302) can also download changes, add-ons, and updates, for instance, to its firmware, software (e.g., including executable instructions, applications, program modules), and operating system.

According to one embodiment, the user computing entity (1302) may include location determining aspects, devices, modules, functionalities, and/or similar words used herein interchangeably. For example, the user computing entity (1302) may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites. The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. Alternatively, the location information can be determined by triangulating the user computing entity's (1302) position in connection with a variety of other systems, including cellular towers, Wi-Fi access points, and/or the like. Similarly, the user computing entity (1302) may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops), and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The user computing entity (1302) may also include a user interface (that can include a display (1312) coupled to a processing element (1306) and/or a user input interface (coupled to a processing element (1306). For example, the user interface may be a user application, browser, user interface, and/or similar words used herein interchangeably executing on and/or accessible via the user computing entity (1302) to interact with and/or cause display of information from the management computing entity (1202), as described herein. The user input interface can include any of a number of devices or interfaces allowing the user computing entity (1302) to receive data, such as a keypad (1316) (hard or soft), a touch display, voice/speech or motion interfaces, or other input device. In embodiments including a keypad (1316), the keypad (1316) can include (or cause display of) the conventional numeric (0-9) and related keys (#, *), and other keys used for operating the user computing entity (1302) and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The user computing entity (1302) can also include volatile storage or memory (1318) and/or non-volatile storage or memory (1320), which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and nonvolatile storage or memory can store databases, database instances, database management systems, data, applications, programs, program modules, scripts, source code, object code, byte code, compiled code, interpreted code, machine code, executable instructions, and/or the like to implement the functions of the user computing entity (1302). As indicated, this may include a user application that is resident on the entity or accessible through a browser or other user interface for communicating with the management computing entity (1202) and/or various other computing entities.

In another embodiment, the user computing entity (1302) may include one or more components or functionality that are the same or similar to those of the management computing entity (1202), as described in greater detail above. As will be recognized, these architectures and descriptions are provided for exemplary purposes only and are not limiting to the various embodiments.

Figure 14:
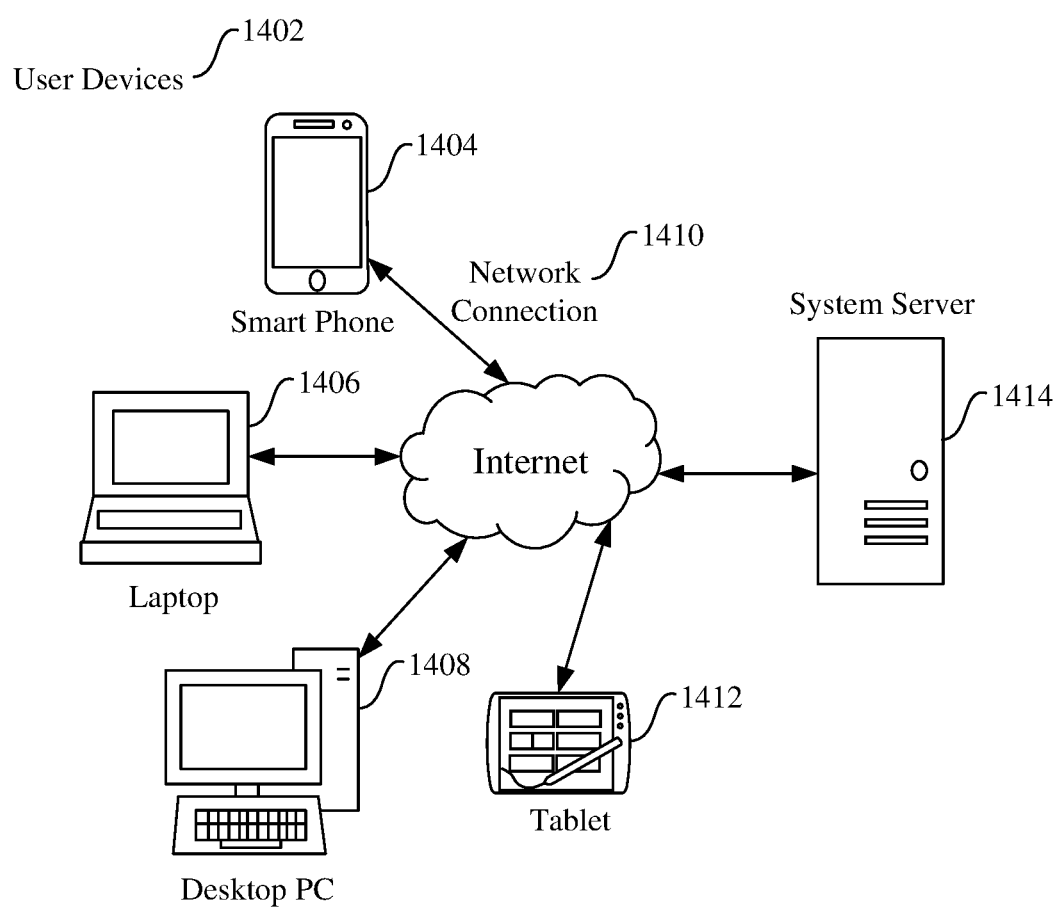
FIG. 14 shows an illustrative system architecture that can be used for predicting a user's body composition in a client-server environment, in conjunction with embodiments of the present invention.

The present invention may be implemented in a client-server environment. FIG. 14 shows an illustrative system architecture for implementing one embodiment of the present invention in a client server environment. User devices (i.e., image-capturing device) (1402) on the client side may include smart phones (1404), laptops (1406), desktop PCs (1408), tablets (1412), or other devices. Such user devices (1402) access the service of the system server (1414) through some network connection (1410), such as the Internet.

In some embodiments of the present invention, the entire system can be implemented and offered to the end-users and operators over the Internet, in a so-called cloud implementation. No local installation of software or hardware would be needed, and the end-users and operators would be allowed access to the systems of the present invention directly over the Internet, using either a web browser or similar software on a client, which client could be a desktop, laptop, mobile device, and so on. This eliminates any need for custom software installation on the client side and increases the flexibility of delivery of the service (software-as-a-service) and increases user satisfaction and ease of use. Various business models, revenue models, and delivery mechanisms for the present invention are envisioned, and are all to be considered within the scope of the present invention.

Additional Implementation Details

Although an example processing system has been described above, implementations of the subject matter and the functional operations described herein can be implemented in other types of digital electronic circuitry, or in computer software, firmware, or hardware, including the structures disclosed in this specification and their structural equivalents, or in combinations of one or more of them.

Embodiments of the subject matter and the operations described herein can be implemented in digital electronic circuitry, or in computer software, firmware, or hardware, including the structures disclosed in this specification and their structural equivalents, or in combinations of one or more of them. Embodiments of the subject matter described herein can be implemented as one or more computer programs, i.e., one or more modules of computer program instructions, encoded on computer storage medium for execution by, or to control the operation of, information/data processing apparatus. Alternatively, or in addition, the program instructions can be encoded on an artificially generated propagated signal, e.g., a machine-generated electrical, optical, or electromagnetic signal, which is generated to encode information/data for transmission to suitable receiver apparatus for execution by an information/data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described herein can be implemented as operations performed by an information/data processing apparatus on information/data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing, and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or information/data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described herein can be performed by one or more programmable processors executing one or more computer programs to perform actions by operating on input information/data and generating output. Processors suitable for the execution of a computer program include, by way of example, both general and special purpose microprocessors, and any one or more processors of any kind of digital computer. Generally, a processor will receive instructions and information/data from a read only memory or a random-access memory or both. The essential elements of a computer are a processor for performing actions in accordance with instructions and one or more memory devices for storing instructions and data. Generally, a computer will also include, or be operatively coupled to receive information/data from or transfer information/data to, or both, one or more mass storage devices for storing data, e.g., magnetic, magneto optical disks, or optical disks. However, a computer need not have such devices. Devices suitable for storing computer program instructions and information/data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described herein can be implemented on a computer having a display device, e.g., a CRT (cathode ray tube) or LCD (liquid crystal display) monitor, for displaying information/data to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described herein can be implemented in a computing system that includes a back end component, e.g., as an information/data server, or that includes a middleware component, e.g., an application server, or that includes a front end component, e.g., a client computer having a graphical user interface or a web browser through which a user can interact with an implementation of the subject matter described herein, or any combination of one or more such back end, middleware, or front end components. The components of the system can be interconnected by any form or medium of digital information/data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits information/data (e.g., an HTML page) to a client device (e.g., for purposes of displaying information/data to and receiving user input from a user interacting with the client device). Information/data generated at the client device (e.g., a result of the user interaction) can be received from the client device at the server.

While this specification contains many specific implementation details, these should not be construed as limitations on the scope of any embodiment or of what may be claimed, but rather as descriptions of features specific to particular embodiments. Certain features that are described herein in the context of separate embodiments can also be implemented in combination in a single embodiment. Conversely, various features that are described in the context of a single embodiment can also be implemented in multiple embodiments separately or in any suitable sub-combination.

Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

In some embodiments of the present invention, the entire system can be implemented and offered to the end-users and operators over the Internet, in a so-called cloud implementation. No local installation of software or hardware would be needed, and the end-users and operators would be allowed access to the systems of the present invention directly over the Internet, using either a web browser or similar software on a client, which client could be a desktop, laptop, mobile device, and so on. This eliminates any need for custom software installation on the client side and increases the flexibility of delivery of the service (software-as-a-service), and increases user satisfaction and ease of use. Various business models, revenue models, and delivery mechanisms for the present invention are envisioned, and are all to be considered within the scope of the present invention.

In general, the method executed to implement the embodiments of the invention, may be implemented as part of an operating system or a specific application, component, program, object, module or sequence of instructions referred to as "computer program(s)" or "computer code(s)." The computer programs typically include one or more instructions set at various times in various memory and storage devices in a computer, and that, when read and executed by one or more processors in a computer, cause the computer to perform operations necessary to execute elements involving the various aspects of the invention. Moreover, while the invention has been described in the context of fully functioning computers and computer systems, those skilled in the art will appreciate that the various embodiments of the invention are capable of being distributed as a program product in a variety of forms, and that the invention applies equally regardless of the particular type of machine or computer-readable media used to actually effect the distribution. Examples of computer-readable media include but are not limited to recordable type media such as volatile and non-volatile memory devices, floppy and other removable disks, hard disk drives, optical disks, which include Compact Disk Read-Only Memory (CD ROMS), Digital Versatile Disks (DVDs), etc., as well as digital and analog communication media.

One of ordinary skill in the art knows that the use cases, structures, schematics, and flow diagrams may be performed in other orders or combinations, but the inventive concept of the present invention remains without departing from the broader scope of the invention. Every embodiment may be unique, and methods/steps may be either shortened or lengthened, overlapped with the other activities, postponed, delayed, and continued after a time gap to practice the methods of the present invention.

Conclusions

Many modifications and other embodiments of the disclosure set forth herein will come to mind to one skilled in the art to which these embodiments pertain having the benefit of the teachings presented in the foregoing descriptions and the associated drawings. Therefore, it is to be understood that the embodiments are not to be limited to the specific embodiments disclosed and that modifications and other embodiments are intended to be included within the scope of the appended claims. Although specific terms are employed herein, they are used in a generic and descriptive sense only and not for purposes of limitation.

Although the present invention has been described with reference to specific exemplary embodiments, it will be evident that the various modification and changes can be made to these embodiments without departing from the broader scope of the invention. Accordingly, the specification and drawings are to be regarded in an illustrative sense rather than in a restrictive sense. It will also be apparent to the skilled artisan that the embodiments described above are specific examples of a single broader invention which may have greater scope than any of the singular descriptions taught. There may be many alterations made in the descriptions without departing from the scope of the present invention.

What is claimed is:

1. A computer-implemented method for predicting a body composition of a user, the method comprising:
   receiving one or more user images, and one or more user parameters;
   generating one or more key points based on the one or more user images; and
   generating a prediction of the body composition of the user based on the one or more key points and the one or more user parameters, using a body composition deep learning network (DLN),
   wherein the body composition is a quantitative measurement of one or more constituent components of the body,
   wherein the body composition DLN was trained to generate predictions of the quantitative measurement of the one or more constituent components of the body, and
   wherein the body composition DLN comprises a face image DLN configured to receive a face image of the user, and to generate a face feature vector; a body feature DLN configured to receive the one or more user parameters and a set of one or more scaled external body feature dimensions, and to generate a body feature vector; and an output DLN configured to receive the face feature vector and the body feature vector, and to generate the body composition of the user.

2. The computer-implemented method of claim 1, wherein the generating one or more key points comprises using a key point DLN.

3. The computer-implemented method of claim 1, wherein the face image DLN is a Convolutional Neural Network (CNN), and the body feature DLN and the output DLN are fully connected neural networks.

4. The computer-implemented method of claim 1, wherein the body composition is an indicator of muscle, bone, water content, or body fat of the user.

5. The computer-implemented method of claim 1, wherein the body composition is selected from the group consisting of a Lean Body Mass (LBM), a Mass Body Fat (MBF), a Soft Lean Mass (SLM), and a Percent Body Fat (PBF).

6. The computer-implemented method of claim 1, wherein the one or more user parameters are selected from the group consisting of a height, a weight, a gender, and an age.

7. The computer-implemented method of claim 1, further comprising:
   extracting a head image of the user from the one or more user images, wherein generating the body composition using the body composition DLN is further based on the head image.

8. The computer-implemented method of claim 7, wherein the head image is a face image, and wherein the face image is extracted using one of a face extraction computer vision module and a face extraction DLN.

9. The computer-implemented method of claim 1, wherein the one or more user images comprise at least a front image and a side image.

10. The computer-implemented method of claim 1, wherein the one or more user images represent a fully clothed user.

11. The computer-implemented method of claim 1, further comprising:
   calculating a height of the user from the one or more user images; and
   utilizing the height as one of the user parameters.

12. The computer-implemented method of claim 1, further comprising:
   calculating a weight of the user from the one or more user images; and
   utilizing the weight as one of the user parameters.

13. The computer-implemented method of claim 1, further comprising:
   generating a set of one or more scaled external body feature dimensions based on the one or more key points, wherein generating the body composition using the body composition DLN is further based on the set of one or more scaled external body feature dimensions.

14. The computer-implemented method of claim 13, wherein the generating the set of one or more scaled external body feature dimensions comprises:
   generating a set of one or more external body feature dimensions from the one or more key points; and
   scaling the set of one or more external body feature dimensions to generate the set of one or more scaled external body feature dimensions.

15. The computer-implemented method of claim 14, wherein the one or more external body feature dimensions are selected from the group consisting of a height, a belly depth, a belly length, a belly waist, a bust girth, a hip girth, a neck girth, a thigh girth, an under bust girth, an upper arm girth, a waist girth, and a wrist girth.

16. A non-transitory storage medium storing program code executable by a hardware processor to predict a body composition of a user, the program code configured to:
- receive one or more user images, and one or more user parameters;
- generate one or more key points based on the one or more user images; and
- generate a prediction of the body composition of the user based on the one or more key points and the one or more user parameters, using a body composition deep learning network (DLN), wherein the body composition is a quantitative measurement of one or more constituent components of the body, and wherein the body composition DLN was trained to generate predictions of the quantitative measurement of the one or more constituent components of the body, and
- wherein the body composition DLN comprises:
- a face image DLN configured to receive a face image of the user, and to generate a face feature vector;
- a body feature DLN configured to receive the one or more user parameters and a set of one or more scaled external body feature dimensions, and to generate a body feature vector; and
- an output DLN configured to receive the face feature vector and the body feature vector, and to generate the body composition of the user.

17. The non-transitory storage medium of claim 16, wherein the generating one or more key points comprises using a key point DLN.

18. A system for predicting a body composition of a user, the system comprising:
- a hardware processor; and
- a non-transitory storage medium, the non-transitory storage medium storing computer-executable program code, which when executed by the hardware processor, causes the hardware processor to execute steps to:
- receive one or more user images, and one or more user parameters;
- generate one or more key points based on the one or more user images; and
- generate a prediction of the body composition of the user based on the one or more key points and the one or more user parameters, using a body composition deep learning network (DLN), wherein the body composition is a quantitative measurement of one or more constituent components of the body, and wherein the body composition DLN was trained to generate predictions of the quantitative measurement of the one or more constituent components of the body, and
- wherein the body composition DLN comprises:
- a face image DLN configured to receive a face image of the user, and to generate a face feature vector;
- a body feature DLN configured to receive the one or more user parameters and a set of one or more scaled external body feature dimensions, and to generate a body feature vector; and
- an output DLN configured to receive the face feature vector and the body feature vector, and to generate the body composition of the user.

* * * * *